United States Patent
O'Daly

(10) Patent No.: US 6,673,351 B1
(45) Date of Patent: Jan. 6, 2004

(54) COMPOSITIONS AND METHODS FOR THE TREATMENT AND CLINICAL REMISSION OF PSORIASIS

(75) Inventor: Jose Antonio O'Daly, Caracas (VE)

(73) Assignee: Astralis, LLC, Florham Park, NJ (US)

( * ) Notice: Subject to any disclaimer, the term of this patent is extended or adjusted under 35 U.S.C. 154(b) by 92 days.

(21) Appl. No.: 09/809,003

(22) Filed: Mar. 16, 2001

(51) Int. Cl.[7] ............................................... A61K 39/00
(52) U.S. Cl. ............................. 424/191.1; 424/265.1; 424/266.1; 424/269.1
(58) Field of Search .................... 424/184.1, 185.1, 424/191.1, 265.1, 269.1, 266.1; 514/2; 530/300, 350, 412, 415, 416, 422, 426

(56) References Cited

U.S. PATENT DOCUMENTS

| | | |
|---|---|---|
| 4,687,666 A | 8/1987 | O'Daly |
| 4,992,273 A | 2/1991 | Monjour et al. |
| 5,202,320 A | 4/1993 | Tidwell et al. |
| 5,411,865 A | 5/1995 | Reed |
| 5,496,830 A | 3/1996 | Shapiro et al. |
| 5,541,196 A | 7/1996 | Fournet et al. |
| 5,658,952 A | 8/1997 | Jacobus |
| 5,674,503 A | 10/1997 | Olafson |
| 5,719,263 A | 2/1998 | Reed |
| 5,726,292 A | 3/1998 | Lowell |
| 5,733,778 A | 3/1998 | Matlashewski et al. |
| 5,767,097 A | 6/1998 | Tam |
| 5,780,591 A | 7/1998 | Matlashewski et al. |
| 5,827,671 A | 10/1998 | Matlashewski et al. |
| 5,834,592 A | 11/1998 | Reed et al. |
| 5,876,735 A | 3/1999 | Reed |
| 5,912,166 A | 6/1999 | Reed et al. |
| 5,965,142 A | 10/1999 | Dillion et al. |
| 6,013,268 A | 1/2000 | Reed |
| 6,027,934 A | 2/2000 | Powell |
| 6,048,530 A | 4/2000 | Srivastava |
| 6,057,142 A | 5/2000 | Aerts |
| 6,063,902 A | 5/2000 | Stiegler |
| 6,087,341 A | 7/2000 | Khavari et al. |
| 6,133,017 A | 10/2000 | Matlashewski et al. |
| 6,139,844 A | 10/2000 | Alkemade et al. |
| 6,162,612 A | 12/2000 | Giordano |
| 6,162,638 A | 12/2000 | Papadopoulou et al. |
| 6,165,735 A | 12/2000 | Chandrashekar et al. |
| 6,168,923 B1 | 1/2001 | Scott et al. |
| 6,174,995 B1 | 1/2001 | Li et al. |

FOREIGN PATENT DOCUMENTS

| | | |
|---|---|---|
| EP | 0135108 | 3/1985 |
| EP | 0276783 A2 | 8/1988 |
| EP | 0293827 A2 | 12/1988 |
| EP | 0703295 A1 | 3/1996 |
| EP | 0806476 A2 | 11/1997 |
| FR | 2570947 A1 | 4/1986 |
| FR | 2612779 A1 | 9/1988 |
| FR | 2615103 A1 | 11/1988 |
| WO | WO 89/01045 | 2/1989 |
| WO | WO 95/06628 | 3/1995 |
| WO | WO 95/30006 | 11/1995 |
| WO | WO 00/39298 | 7/2000 |

OTHER PUBLICATIONS

O'Daly Carbonell, JA, et al., Proteinas de amastigotes de varias especies de leishmanias protegen a seres humanos contra la leishmaniasis en el area endemica de Guatire, Estado Miranda, Venezuela, Gaceta Medica De Caracas,vol. 103, No. 2, Apr.–Jun. 1995, pp. 141–143, Materials and Methods.

J.A. O'Daly, et al., "Differential growth requirements of several Leishmania spp. in chemically defined culture media," Acta Tropica—Journal of Biomedical Sciences, 1988, 45, pp. 109–126.

Primary Examiner—Patricia A. Duffy
(74) Attorney, Agent, or Firm—Michael P. Williams; Bond, Schoeneck & King, PLLC

(57) ABSTRACT

Polypeptides comprising amino acid sequences of particulate antigens isolated from various species of Leishmania protozoa, or immunogenic variants thereof, are disclosed for the treatment and clinical remission of psoriasis. Also disclosed are nucleic acid sequences encoding such polypeptides, vectors incorporating such nucleic acid sequences, methods for genetically engineering microbial host cells to produce such polypeptides, and such recombinant microbial host cells. In another embodiment, immunotherapeutic agents incorporating the polypeptides or the nucleic acid sequences are disclosed for the treatment and clinical remission of psoriasis. In another embodiment, methods for the production of the polypeptides using recombinant microbial host cells are disclosed. Finally, methods for the treatment and clinical remission of psoriasis comprising administration of a pharmaceutical composition comprising one or more of the polypeptides or one or more of the nucleic acid sequences are disclosed. The polypeptides induced a TH1 cellular immune response, a positive intradermic reaction, and a blastogenic response in peripheral blood lymphocytes after clinical remission of lesions. Populations of peripheral blood lymphocytes that are altered in psoriasis patients returned to normal values in patients who received the polypeptides and experienced clinical remission of lesions after treatment.

18 Claims, No Drawings

COMPOSITIONS AND METHODS FOR THE TREATMENT AND CLINICAL REMISSION OF PSORIASIS

FIELD OF THE INVENTION

The present invention relates generally to immunotherapeutic agents or therapeutic agents, compositions comprising those agents, and methods of use of those agents and compositions for the treatment and clinical remission of psoriasis.

BACKGROUND

Psoriasis is a chronic, genetically-influenced, remitting and relapsing scaly and inflammatory skin disorder of unknown etiology that affects 1 to 3 percent of the world's population. There are several types of psoriasis, including plaque, pustular, guttate and arthritic variants. There is at present no cure for psoriasis, but rather only suppressive therapy (Greaves and Weinstein, 1995, Drug Therapy, 332: 581–588). Indications for treatment may arise from local symptoms, for example, pain, itching, reduction of manual dexterity, severe problems with walking, and cosmetic problems such as prominent hand, leg, or facial lesions. Due to the toxicity of the available therapies, patients with limited disease will often decide to forego treatment beyond the avoidance of provoking factors.

The goal of current treatments has been to decrease the severity and extent of psoriasis to the point at which it no longer interferes substantially with the patient's occupation, well-being, or personal or social life. The initial treatment for stable plaque psoriasis of any severity is topical. In patients in which more than 20 percent of the skin is affected, however, topical treatment alone may be impractical and systemic therapy may also be indicated at the outset.

The topical treatment for plaque psoriasis incorporates the use of emollients, keratolytic agents, coal tar, anthralin, corticosteroids of medium to strong potency, and calpotriene. All of these treatments have variable efficacy, fail to prevent frequent relapses of the disease, exhibit side effects, and pose cosmetic problems of their own.

Systemic treatment has been used in patients with physically, socially, or economically disabling psoriasis that has not responded to topical treatment. The choices to date have been phototherapy or systemic drug therapy. Generally, systemic treatment has employed phototherapy with Ultraviolet B irradiation, photo chemotherapy which combines the photosensitizing drug methoxsalen with Ultraviolet A phototherapy (PUVA), methotrexate, etretinate, systemic corticosteroids, and cyclosporine. Each of these systemic treatments has variable efficacy and undesired side effects, and some of them are very toxic and present frequent relapses of the disease. Accordingly, there is at present a need for an effective psoriasis treatment that avoids the disadvantages associated with the currently available topical or systemic treatments.

SUMMARY OF THE INVENTION

The present invention provides compositions and methods for the treatment and clinical remission of psoriasis. In one aspect, polypeptides derived from particulate antigens of protozoans of the genus Leishmania are provided that can generate an immune is response in an individual resulting in abatement of the clinical symptoms of psoriasis. In one embodiment of this aspect, the polypeptides comprise at least one of the amino acid sequences recited in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14, or immunogenic variants thereof. An immunogenic variant of an amino acid sequence may be either a truncated version of the sequence that retains a substantial amount of the activity of the original, or an altered version of the sequence retaining such activity and having conservative amino acid substitutions and/or modifications.

In another embodiment of this aspect, the polypeptides comprise at least an immunogenic portion of an amino acid sequence of a protein, or an immunogenic variant thereof, the protein isolated from protozoans of the genus Leishmania and having an apparent molecular weight of 21, 33, 44, 50, 55, 58, 65, or 77 kDa as determined by sodium dodecyl-sulfate polyacrylamide gel electrophoresis (SDS-PAGE).

In yet another embodiment of this aspect, the polypeptides comprise at least an immunogenic portion of an amino acid sequence of a protein, or an immunogenic variant thereof, the protein isolated from protozoans of the genus Leishmania and having an apparent molecular weight after total reduction and alkylation of 73, 80, or 82 kDa as determined by SDS-PAGE.

In related aspects, the present invention provides nucleic acid sequences encoding such polypeptides, vectors incorporating such nucleic acid sequences, methods for the production of such polypeptides by transformation, transfection, or transduction of microbial host cells, and microbial host cells transformed by such vectors, transfected by such nucleic acid sequences, or transduced with such nucleic acid sequences.

In another aspect of the invention, immunotherapeutic agents incorporating one or more polypeptides of the present invention are provided. These immunotherapeutic agents may be polyvalent or monovalent, and may incorporate an adjuvant such as alumina to enhance the immune response obtained from an inoculated subject. In a preferred embodiment, the polyvalent immunotherapeutic agent contains polypeptide isolates from a mixture of four species of Leishmania, namely, *L.(L)amazonensis, L.(L)venezuelensis, L.(V)brasiliensis,* and *L.(L)chagasi*. Also in a preferred embodiment, the monovalent immunotherapeutic agent contains a polypeptide isolate from one of these four species.

In another aspect of the invention, methods for the treatment and clinical remission of psoriasis are provided. In one embodiment, such a method involves administration of a therapeutically effective amount of a pharmaceutical composition comprising one or more polypeptides of the present invention to a subject in order to induce an immune response resulting in abatement of the clinical symptoms of psoriasis. In a related embodiment, the method involves administration of a therapeutically effective amount of a pharmaceutical composition comprising one or more nucleic acid sequences of the present invention to a subject. The term "therapeutically effective" as used herein means a reduction of approximately 70–100% of Psoriasis Area and Severity Index as is understood by those skilled in the art.

Other aspects of the invention include the use of the nucleic acid sequences of the invention as probes for genetic analysis and as nucleic acid molecular weight markers, and the use of the polypeptides of the invention as molecular weight markers.

DETAILED DESCRIPTION OF THE INVENTION

The present invention concerns novel compositions and methods for the treatment and clinical remission of psoriasis. The compositions comprise immunogenic polypeptides or the nucleic acids encoding them. The polypeptides of the present invention can elicit an immune response in a warm-blooded animal, thereby inducing clinical remission of psoriasis. As used herein, the term "warm-blooded animal" includes humans. In one embodiment of the invention, the subject polypeptides can be isolated from Leishmania protozoa and, preferably, from killed Leishmania amastigote protozoa. The polypeptides of the subject invention can be obtained from protozoa of the Leishmania genus using standard protein isolation procedures which are known in the art. Also contemplated by the present invention are immunotherapeutic agents and pharmaceutical compositions incorporating the immunogenic polypeptides of the present invention. In one embodiment, a first-generation polyvalent immunotherapeutic agent is provided, comprising a polypeptide isolate of a mixture of a plurality of Leishmania species, such as *L.(L)amazonensis, L.(L) venezuelensis, L.(V)brasiliensis, L.(L)chagasi, L.(L) donovani, L.(L)infantum, L.(L)major, L.(L)panamensis, L.(L)tropica*, and *L.(L)guyanensis*. Preferably, the mixture comprises *L.(L)amazonensis, L.(L)venezuelensis, L.(V) brasiliensis*, and *L.(L)chagasi*. Most preferably, the mixture consists of these four species. The organisms are preferably cultivated in the amastigote stage in the synthetic culture medium specified in Table 1, supplemented with 5% fetal bovine serum, typically at about 30–34° C. Subsequently, and during the stationary phase of growth, the amastigotes are subjected to a medium containing an amount of N-p-tosyl-L-Lysine chloromethyl ketone (TLCK) or a pharmacologically acceptable salt thereof effective to kill the cells. The dead cells are then isolated and treated with the non-ionic detergent Nonidet p-40 (NP40) to solubilize the surface antigens, which are discarded. The particulate antigens that comprise the immunogenic polypeptides of the present invention can be collected by centrifugation following cell disruption. These polypeptides are washed with phosphate-buffered saline (PBS) and subsequently resuspended by sonication for 5 minutes at 4° C. in PBS containing alumina.

In another embodiment, a first-generation monovalent immunotherapeutic agent is described, comprising a polypeptide isolate of a single Leishmania species chosen from the group consisting of *L.(L)amazonensis, L. (L)venezuelensis, L.(V)brasiliensis, L.(L)chagasi, L.(L) donovani, L.(L)infantum, L.(L)major, L. (L)panamensis, L.(L)tropica*, and *L.(L)guyanensis*. Preferably, the single Leishmania species is chosen from the group consisting of *L.(L)amazonensis, L.(L)venezuelensis, L.(V)brasiliensis*, and *L.(L)chagasi*. Procedures for the preparation of this immunotherapeutic agent are otherwise identical to those disclosed above for the first-generation polyvalent immunotherapeutic agent.

In another embodiment, a second-generation polyvalent immunotherapeutic agent is described, comprising a polypeptide isolate of a mixture of a plurality of Leishmania species, such as *L.(L)amazonensis, L.(L)venezuelensis, L. (V)brasiliensis, L.(L)chagasi, L.(L)donovani, L.(L)infantum, L. (L)major, L.(L)panamensis, L.(L)tropica*, and *L.(L) guyanensis*. Preferably, the mixture comprises *L.(L) amazonensis, L.(L)venezuelensis, L.(V)brasiliensis*, and *L.(L)chagasi*. Most preferably, the mixture consists of these four species. The organisms are preferably cultivated in the amastigote stage in the synthetic culture medium specified in Table 1, supplemented with 5% fetal bovine serum, typically at about 30–34° C. Subsequently, and during the stationary phase of growth, the amastigotes are subjected to a medium containing an amount of N-p-tosyl-L-Lysine chloromethyl ketone (TLCK) or a pharmacologically acceptable salt thereof effective to kill the cells. The dead cells are then isolated and treated with the non-ionic detergent Nonidet p-40 (NP40) to solubilize the surface antigens, which are discarded. The particulate antigens that comprise the immunogenic polypeptides of the present invention can be collected by centrifugation following cell disruption. These polypeptides are washed with phosphate-buffered saline (PBS) and subsequently resuspended by sonication for 5 minutes at 4° C. in 8 M Urea, 0.025 M Tris (Tris-hydroxy-methyl-amino-methane). The polypeptides are then subjected to chromatography on a DEAE-Sephadex column with a stepwise elution from 0.05–0.3 M NaCl in a solution containing 8 M Urea, 0.025 M Tris, pH 8.3. Seven protein fractions are collected, and an inoculum comprising each protein fraction is made by resuspending the polypeptides of each fraction in PBS containing alumina.

In another embodiment, a second-generation monovalent immunotherapeutic agent is described, comprising a polypeptide isolate of a single Leishmania species chosen from the group consisting of *L.(L)amazonensis, L.(L) venezuelensis, L.(V)brasiliensis, L.(L)chagasi, L.(L) donovani, L.(L)infantum, L.(L)major, L.(L)panamensis, L.(L)tropica*, and *L.(L)guyanensis*. Preferably, the single Leishmania species is chosen from the group consisting of *L.(L)amazonensis, L.(L)venezuelensis, L.(V)brasiliensis*, and *L.(L)chagasi*. Procedures for the preparation of this immunotherapeutic agent are otherwise identical to those disclosed above for the second-generation polyvalent immunotherapeutic agent.

Alternatively, the subject polypeptides can be synthesized according to known procedures and techniques, or produced recombinantly by taansforming a host cell with one or more of the nucleotide sequences encoding the desired polypeptides. The polypeptides can be expressed in the host cell such that they can be isolated and purified to a desired degree of purification. The subject polypeptides can be used in accordance with the subject invention as a third-generation immunotherapeutic agent to treat psoriasis.

The instant invention further concerns nucleic acid sequences that can be useful in transforming appropriate host cells to cause them to produce the polypeptides of the invention; in administration to a warm-blooded animal, either directly or as part of a pharmaceutically-acceptable composition, to generate an immune response and thereby induce clinical remission of psoriasis in the animal; as labelled probes for genetic analysis; or as nucleic acid molecular weight markers.

One of ordinary skill in the art of molecular biology can obtain nucleic acids encoding the polypeptides of the present invention in view of the teachings provided herein. For example, the polypeptides of the first-generation immunotherapeutic agent of the present invention have been isolated and purified from protozoa of the Leishmania genus and comprise eight bands, identified by SDS-PAGE, representing eight distinct polypeptides having apparent molecular weights of 21, 33, 44, 50, 55, 58, 65, and 77 kDa, respectively. Each of these bands represents a separate polypeptide that can be isolated and sequenced in accordance with standard amino acid sequencing procedures. The polypeptides of each second-generation immunotherapeutic agent were purified by subjecting the first-generation immunotherapeutic agent containing the mixture of eight polypeptides to chromatography on diethylaminoethyl(DEAE)-Sephadex. Two fractions having all the activity to cure psoriasis were isolated and totally reduced and alkylated by standard procedures. These fractions were subjected to electrophoresis on acrylamide gels to separate the constituent polypeptides, and the amino acid sequence of each polypeptide was obtained by standard protein sequencing procedures. The nucleotide sequences encoding each of these polypeptides can be derived from these amino acid sequences by application of the genetic code.

Additionally, the present invention contemplates the production of large quantities of the immunogenic polypeptides of the invention via introduction of the nucleic acids encoding them to microbial host cells. The nucleic acids can be introduced directly into the genome of the host cell or can first be incorporated into a vector which is then introduced into the host. Exemplary methods of direct incorporation include transduction by recombinant phage or cosmids, transfection where specially treated host bacterial cells can be caused to take up naked phage chromosomes, and transformation by calcium precipitation. These methods are well known in the art.

Exemplary vectors include plasmids, cosmids, and phages. A genomic library for a Leishmania species can be created by routine means, and DNA of interest isolated therefrom. For example, DNA of Leishmania protozoa can be isolated and restricted with known restriction enzymes. The resulting DNA fragments can then be inserted into suitable cloning vectors for introduction to a compatible host. Depending on the contemplated host, the vector may include various regulatory and other regions, usually including an origin of replication, one or more promoter regions, and markers for the selection of transformants. In general, the vectors will provide regulatory signals for expression and amplification of the DNA of interest.

Various markers may be employed for the selection of transformants, including biocide resistance, particularly to antibiotics such as ampicillin, tetracycline, trimethoprim, chloramphenicol, and penicillin; toxins, such as colicin; and heavy metals, such as mercuric salts. Alternatively, complementation providing an essential nutrient to an auxotrophic host may be employed.

Hosts which may be employed according to techniques well known in the art for the production of the polypeptides of the present invention include unicellular microorganisms, such as prokaryotes, i.e., bacteria; and eukaryotes, such as fungi, including yeasts, algae, protozoa, molds, and the like, as well as plant cells, both in culture or in planta. Specific bacteria which are susceptible to transformation include members of the Enterobacteriaceae, such as strains of *Escherichia coli*; Salmonella; Bacillaceae, such as *Bacillus subtilis*; Pneumococcus; Streptococcus; *Haemophilus influenzae*, and yeasts such as Saccharomyces, among others. As used herein, the term microbial host cell encompasses all of these prokaryotic and eukaryotic organisms, including plant cells, both in culture and in planta.

Universal probes can be obtained which hybridize with certain of the fragments of a DNA library, allowing identification and selection (or "probing out") of the genes of interest, i.e., those nucleotide sequences which encode the polypeptides described as part of the present invention. The isolation of these genes can be performed using techniques which are well known in the art of molecular biology. The isolated genes can be inserted into appropriate vectors for use in the transformation of microbial host cells. In addition, these genes can be subjected to standard nucleic acid sequencing procedures to provide specific information about the nucleotide sequence of the genes encoding the subject polypeptides.

It is now well known in the art that when synthesizing a gene for improved expression in a host cell it is desirable to design the gene such that its frequency of codon usage approaches the frequency of preferred codon usage of the host cell. For purposes of the subject invention, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell.

Thus, in one embodiment of the subject invention, bacteria, plants, or other cells can be genetically engineered, e.g., transformed with genes from protozoa of the Leishmania spp., to attain desired expression levels of the subject polypeptides or proteins. To provide genes having enhanced expression, the DNA sequence of the gene can be modified to comprise codons preferred by highly expressed genes to attain an A+T content in nucleotide base composition which is substantially that found in the transformed host cell. It is also preferable to form an initiation sequence optimal for said host cell, and to eliminate sequences that cause destabilization, inappropriate polyadenylation, degradation and termination of RNA and to avoid sequences that constitute secondary structure hairpins and RNA splice sites. For example, in synthetic genes, the codons used to specify a given amino acid can be selected with regard to the distribution frequency of codon usage employed in highly expressed genes in the host cell to specify that amino acid. As is appreciated by those skilled in the art, the distribution frequency of codon usage utilized in the synthetic gene is a determinant of the level of expression.

Assembly of the genes of this invention can be performed using standard technology known in the art. A structural gene designed for enhanced expression in a host cell can be enzymatically assembled within a DNA vector from chemically synthesized oligonucleotide duplex segments. The gene can then be introduced into the host cell and expressed by means known in the art. Preferably, the protein produced upon expression of the synthetic gene is functionally equivalent to a native protein. According to the subject invention, "functionally equivalent" refers to identity or near identity of function. A synthetic gene product which has at least one property relating to its activity or function that is similar or identical to a natural protein is considered functionally equivalent thereto.

It is also well known in the art that the nucleotide sequences of the subject invention can be truncated such that certain of the resulting fragments of the original full-length sequence can retain the desired characteristics of the full-length sequence. A wide variety of restriction enzymes are well known by those skilled in the art to be suitable for generating fragments from larger nucleic acid molecules. For example, it is well known that Ba131 exonuclease can be conveniently used for time-controlled limited digestion of DNA. See, for example, Maniatis et al. (1982) *Molecular Cloning: A Laboratory Manual*, Cold Spring Harbor Laboratory, New York, pages 135–139. See also Wei et al. (1983) *J Biol. Chem.* 258:13006–13512. Thus, Ba131 exonuclease (commonly referred to as "erase-a-base" procedures) allows for the removal of nucleotides from either or both ends of the subject nucleic acids, consequently generating a wide spectrum of fragments, many of which encode products that are functionally equivalent to the natural polypeptide sequences of the present invention. Labeling procedures are also well known, and the ordinarily skilled artisan could routinely screen the labeled fragments for their hybridization characteristics to determine their utility as probes. For example, it is routine to label nucleic acids for use as specific and selective probes in genetic identification or diagnostic procedures. A person of ordinary skill in the art would recognize that variations or fragments of those sequences, which specifically and selectively hybridize to the DNA of Leishmania spp., could also function as a probe. It is within the ordinary skill of persons in the art, and does not require undue experimentation, to determine whether a segment of the subject nucleic acids is a fragment or variant which specifically and selectively hybridizes in accordance with the subject invention. Therefore, fragments or variants of these nucleic acids can be useful as probes to identify, diagnose, or distinguish Leishmania species.

It would also be recognized that the polynucleotides or peptides of the subject invention can be useful as molecular weight markers in respective nucleic acid or amino acid molecular weight determinations or assays.

In order to obtain a first-generation immunotherapeutic agent according to the subject invention, organisms of the genus Leishmania can be cultivated in synthetic culture medium comprising the ingredients listed in Table 1. In a preferred embodiment, the culture medium is supplemented with 5% fetal bovine serum. Cultivation of the protozoa according to the subject invention is typically carried out at about 30–34° C. In a particularly preferred embodiment, cultivation of the protozoa is carried out in the amnastigote stage of its life cycle.

TABLE 1

Leishmania culture medium.

| Ingredient | mg/lt | Ingredient | mg/lt |
|---|---|---|---|
| Methionine | 140 | Carnosine | 25 |
| Tryptophan | 50 | Citrulline | 50 |
| α-Amino Adipic Acid | 3 | Sarcosine | 57 |
| Asparagine | 165 | $CaCl_2$ | 265 |
| Cystine | 47 | $Fe(NO_3)9H_2O$ | 0.72 |
| Histidine | 6 | KCl | 400 |
| Aspartic Acid | 120 | $MgSO_47H_2O$ | 200 |
| Alanine | 512 | NaCl | 5,850 |
| Proline | 248 | $NaHCO_3$ | 2,000 |
| Lysine | 337 | $NaH_2PO_4H_2O$ | 140 |
| Taurine | 6 | Tricine | 900 |
| Isoleucine | 191 | Hemin | 1 |
| Ornithine | 3 | HEPES | 2,000 |
| Tyrosine | 210 | Glucose | 1,000 |
| β-alanine | 80 | D-ribose | 10 |
| Phosphoserine | 23 | 2-Deoxy-ribose | 10 |
| α-amino Butyric Acid | 8 | Cholecalciferol($D_3$) | 0.1 |
| Leucine | 440 | Biotin | 1 |
| Arginine | 413 | Pyridoxamine | 0.05 |
| Serine | 220 | Pyridoxal | 1 |
| Hydroxylysine | 12 | Cyanocobalamin($B_{12}$) | 0.01 |
| Glutamine | 164 | Choline | 1 |
| Glutamic Acid | 420 | Thiamine ($B_1$) | 1 |
| Cysteine | 0.5 | Inositol | 2 |
| Phosphoethanolamine | 25 | α-Tocopherol | 0.01 |
| Threonine | 200 | 3-phytylmenadione($K_1$) | 0.01 |
| Glycine | 235 | Menadione ($K_3$) | 0.01 |
| Phenylalanine | 240 | Retinol (A) | 0.14 |
| Valine | 266 | Riboflavin ($B_2$) | 0.1 |
| d-Pantothenic Acid | 1 | 6,8 Thiotic Acid | 0.01 |
| Ascorbic Acid | 0.05 | Pyridoxine ($B_6$) | 0.025 |
| p-Aminobenzoic Acid | 0.05 | Folic Acid | 1 |
| Ergocalciferol ($D_2$) | 0.1 | Niacinamide | 1 |

TABLE 1-continued

Leishmania culture medium.

| Ingredient | mg/lt | Ingredient | mg/lt |
|---|---|---|---|
| L-carnitine | 0.05 | Tetrahydrofolic Acid | 0.5 |
| DL-methionine-S-methyl-sulfonium chloride (U) | 0.05 | Adenosine-5-Triphosphate (ATP) | 5.5 |
| 2-Deoxyadenylic acid (d-AMP) | 3.0 | 2'-Deoxyuridine-5-monophosphate (d-UMP) | 3.0 |
| 5'-Thymidylic Acid (TMP) | 3.0 | 5'-Deoxyguanylic Acid (d-GMP) | 3.0 |
| 2'Deoxycitidine-5-monophosphate (d-CMP) | 3.0 | Hydroxyproline | 262.5 |

The culture medium comprising the protozoan cells can then be treated in order to inactivate, and preferably kill, the cells. Upon isolation of those cells, the antigenic proteins can be purified therefrom and included in a pharmaceutically acceptable carrier, e.g., buffer solution, to create a second-generation immunotherapeutic agent. Preferably, the cells are inactivated or killed with a non-lysing agent, e.g., TLCK. The antigenic proteins of the present invention are particulate proteins that can be isolated from the cells using accepted methods. In a more specific embodiment the method of creating the second-generation immunotherapeutic agent of the present invention comprises the steps of (1) cultivating to protozoa, preferably in the amastigote stage, in an appropriate culture medium; (2) treating said protozoan cells to inactivate or kill the cells; (3) isolating the treated cells; (4) extracting antigenic proteins from the isolated cells; and (5) formulating the second-generation immunotherapeutic agent composition by combining one or more isolated antigenic proteins with a pharmaceutically acceptable carrier, e.g., phosphate buffered saline (PBS). A preferred pharmaceutically acceptable carrier is a PBS solution having alumina present within the solution.

To cure psoriasis in patients with clinical and histopathological diagnosis of the disease, the first-generation polyvalent immunotherapeutic agent was administered intramuscularly, in the deltoid region, once a month, once every 15 days or once a week according to disease severity, for 7.6±6.0 months on average, at 500 μg/dose.

Furthermore to cure psoriasis a monovalent immunotherapeutic agent with each one of the Leishmania spp. present in the first-generation polyvalent immunotherapeutic agent was used as a subject composition with similar results to the polyvalent immunotherapeutic agent.

Furthermore to cure psoriasis a second-generation immunotherapeutic agent containing the protein fractions isolated by chromatographic means from the crude first-generation immunotherapeutic agent together with 0.1 ml alumina/mg protein was administered intramuscularly in the deltoid region once every 15 days for 3–4 doses at 200 μg/dose in 0.5 ml.

Following are examples which illustrate procedures for practicing the invention. These examples should not be construed as limiting. All percentages are by weight and all solvent mixture proportions are by volume unless otherwise noted.

EXAMPLE 1

Preparation of the Immunogen

Organisms of the genus leishmania are cultivated in the amastigote stage in the synthetic culture medium specified in Table 1, supplemented with 5% fetal bovine serum typically at about 30–34° C. (O'Daly et al., 1988, *Acta Tropica (Basel)*, Vol. 45, pp. 109–126). For the second-generation immunotherapeutic agent, amastigotes at the stationary phase of growth were collected by centrifugation (800 xg for 20 minutes at 4° C.), washed in Phosphate Buffered Saline (PBS), and incubated for 3 days at 30–34° C. in Eagle's MEM (Gibco) containing 150 μg of TLCK to inactivate the parasites as described (O'Daly et al., 1986, *Acta Tropica (Basel)*, Vol. 43, pp. 225–236). After two washes with PBS (12.100×g for 10 minutes at 4° C.) 1×10$^8$ parasites/ml were incubated in MEM containing 0.12% Nonidet-P-40 (NP40, Sigma) for 30 minutes at 4° C. to solubilize the surface antigens which were discarded (O'Daly et al., 1990 *AM J Trop. Med. Hyg.*, Vol. 43, pp. 44–51). Particulate antigens were collected by centrifugation (12.100×g for 10 minutes at 4° C.), washed twice with PBS and sonicated for 5 minutes at 4° C. in a Sonifier Cell Disrupter (Model WI 85, Heath-Systems-Ultrasonic, Inc., Plainview, N.Y.) at the microtip limit of the output control at 50W. Protein content was determined by the method of Lowry (Lowry, O. et al, 1951, *J Biol. Chem.*, Vol. 193, pp. 265–275). The final monovalent first generation immunogen preparation contained 1 mg/ml of each Leishmania spp. antigens in PBS containing alumina (Aluminum hydroxide low viscosity gel REHYDRAGEL, Reheis Inc., New Jersey) at a concentration of 0.1 ml/mg (v/w) of parasite protein. Each step in the preparation of the immunogen was checked for sterility.

In another embodiment of the subject invention, particulate antigens were collected by centrifugation (12.100×g for 10 minutes at 4° C.), washed twice with PBS, dissolved in a solution containing 8 Molar Urea, 0.025 Tris (Tris-hydroxy-methyl-amino-methane) and sonicated for 5 minutes at 4° C. in a Sonifier Cell Disrupter (Model WI 85, Heath-Systems-Ultrasonic, Inc., Plainview, N.Y.) at the microtip limit of the output control at 50W. Protein fractions were separated by DEAE-chromatography.

The second-generation immunotherapeutic agent was prepared with each one of the seven protein fractions isolated after DEAE-chromatography of the subject composition containing only one leishmania specie as for example L.(V) brasiliensis or any other leishmania specie present in the crude first-generation immunotherapeutic agent. Protein content was determined by the method of Lowry (Lowry, O. et al, 1951, *J Biol. Chem.*, Vol. 193, pp. 265–275). Each protein fraction was dissolved in PBS and sonicated for 5 minutes at 4° C. in a Sonifier Cell Disrupter (Model WI 85, Heath-Systems-Ultrasonic, Inc., Plainview, N.Y.) at the microtip limit of the output control at 50W. Subsequently each fraction was filter-sterilized through 0.20 μm Millipore® filters. The final immunogen preparation contained 400 μg/ml of each of the antigenic fractions in PBS containing alumina (Aluminum hydroxide low viscosity gel REHYDRAGEL, Reheis Inc., New Jersey) at a concentration of 0.1 ml/mg (v/w) of the protein fraction. Each step in the preparation of the second generation immunogen was also checked for sterility.

Aliquots were incubated in ESM containing 5% Fetal Bovine Serum (FBS, Gibco) and in agar plates containing 12.5% (w/v) Bacto-Peptone (Difco), 12.5% (w/v) yeast extract (Becton Dickinson), 3.75% (w/v) glucose, and 3.75% (w/v) BBL agar (Becton Dickinson). Samples were incubated for 72 hours at 37° C. to detect fast growing bacteria and for 3 weeks at 26° C. for slow growing bacteria and fungus. Each batch of the immunogen was controlled by SDS-polyacrylamide gel electrophoresis to ensure consistency in the pattern of Leishmania protein bands. Each batch from the first and second generation immunotherapeutic agents was also tested with E-TOXATE (Sigma) for the presence of pyrogens. The first-generation immunogen was stable at 4° C. for at least 4 weeks.

EXAMPLE 2

Protein Components of the Immunogen

From the immunogen preparations obtained from the procedures described in Example 1 above, eight protein bands were identified via SDS-polyacrylamide gel electrophoresis of the TLCK-treated NP-40-extracted amastigotes from *Leishmania(L)amazonensis, Leishmania(L) venezuelensis, Leishmania(V)brasiliensis*, and *Leishmania (L)chagasi*, with apparent molecular weights of 21, 33, 44, 50, 55, 58, 65, and 77 kDa. In untreated entire amastigote extracts between 28 and 30 bands with molecular weights ranging from 29 to 96 kDa were observed in each Leishmania species, and major bands of 29, 34, 43, 58, and 65 kDa were observed.

The immunogen preparations of the second-generation immunotherapeutic agent, which contain protein fractions 3 and 4 obtained after DEAE-chromatography and total reduction and alkylation, had three bands with molecular weights of 73, 80, and 82 kDa.

EXAMPLE 3

Safety and Immunogenicity

The immunogenic composition comprising the proteins of the second-generation immunotherapeutic agent, described in Examples 1 and 2, above, was injected into a human volunteer at monthly intervals, beginning with 50 μg and increasing the dose by 50 μg each month, in order to determine the dose capable of inducing an IDR greater than 5 mm. This dose was found to be 200 μg. At both one month and six months after the last dose of immunotherapeutic agent, the following blood tests were performed on this volunteer: complete blood count; differential white blood cell count; urea; creatinin; sugar alkaline phosphatase; bilirubin; transaminases; cholesterol; triglycerides; C reactive protein; serological tests such as VDRL, HIV, antinuclear antibodies, LE cells; and urine and fecal analysis. All the values were within normal limits, and no side effects were observed.

EXAMPLE 4

Preparation of Immunotherapeutic Agent Compositions

For the first-generation monovalent immunotherapeutic agent, cultivated amastigotes of each species of Leishmania were collected by centrifugation (800×g for 20 minutes at 4° C.), washed in Phosphate Buffered Saline (PBS) and incubated for 3 days at 30–34° C. in Eagles's MEM (Gibco) containing 150 μg of TLCK to inactivate the parasites as described, at 1×10$^8$ parasites/ml. This step is preferably carried out when the amastigotes are in the stationary growth phase, after two washes with PBS (12.100×g for 10 minutes at 4° C.).

In a particularly preferred embodiment, preparation of a protective monovalent first generation immunogenic composition according to the subject invention comprises the following steps:

A) cultivating organisms of the genus Leishmania in the amastigote state in a synthetic culture medium containing the ingredients listed in Table 1 supplemented with 5% fetal bovine serum typically at about 30–34° C.;

B) subjecting organisms of the genus Leishmania in the arnastigote stage, and at the stationary phase of growth, to a medium containing an amount of N-p-tosyl-L-Lysine chloromethyl ketone or a pharmacologically acceptable salt thereof effective to kill said cells;

C) isolating said killed cells;

D) extracting the surface proteins with the non-ionic detergent Nonidet p-40;

E) centrifugation of the preparation to isolate particulate antigens;

F) washing twice with PBS; and

G) forming an immunizing inoculum comprising said particulate antigens from said killed cells by resuspending them in phosphate buffered saline comprising alumina.

For the second generation immunotherapeutic agent composition, cultivated arnastigotes were collected by centrifugation (800×g for 20 minutes at 4° C.), washed in Phosphate Buffered Saline (PBS) and incubated for 3 days at 30–34° C. in Eagles's MEM (Gibco) containing 150 $\mu$g of TLCK to inactivate the parasites as described, at $1\times10^8$ parasites/ml. This step is preferably carried out when the amastigotes are in the stationary growth phase, after two washes with PBS (12.100×g for 10 minutes at 4° C.).

In a particularly preferred embodiment, preparation of a protective second generation immunogenic composition according to the subject invention comprises the following steps:

A) cultivating organisms of the genus Leishmania in the amastigote state in a synthetic culture medium containing the ingredients listed in Table 1 supplemented with 5% fetal bovine serum typically at about 30–34° C.;

B) subjecting organisms of the genus Leishmania in the amasfigote stage and at the stationary phase of growth, to a medium containing an amount of N-p-tosyl-L-Lysine chloromethyl ketone or a pharmacologically acceptable salt thereof effective to kill said cells;

C) isolating said killed cells;

D) extracting the surface proteins with the non-ionic detergent Nonidet p-40;

E) centrifugation of the preparation to isolate particulate antigens;

F) washing twice with PBS,

G) dissolving in a solution containing 8 Molar Urea, 0.025 Molar Tris (Tris-hydroxy-methyl-amino-methane) and sonicating for 5 minutes at 4° C. in a Sonifier Cell Disrupter (Model WI 85, Heath-Systems-Ultrasonic, Inc., Plainview, N.Y.) at the microtip limit of the output control at 50W.

H) separating protein fractions in a DEAE-Sephadex column with a NaCl stepwise elution from 0.05–0.3 Molar NaCl concentration in a solution containing 8 Molar Urea, 0.025 Molar Tris pH 8.3; and I) forming an immunizing inoculum comprising said particulate antigens from said killed cells by resuspending them in phosphate buffered saline comprising alumina.

In a particularly preferred embodiment, preparation of an immunogenic composition for clinical remission of psoriasis according to the second-generation subject invention comprises the following steps:

A) cultivating organisms of the genus Leishmania in the amastigote state in a synthetic culture medium containing the ingredients listed in Table 1 supplemented with 5% fetal bovine serum typically at about 34° C.;

B) subjecting organisms of the genus Leishmania in the amastigote stage and at the stationary phase of growth, to a medium containing an amount of N-p-tosyl-L-Lysine chloromethyl ketone or a pharmacologically acceptable salt thereof effective to kill said cells;

C) isolating said killed cells;

D) extracting the surface proteins with the non-ionic detergent Nonidet p-40;

E) DEAE Sephadex chromatography of particulate antigens from only one Leishmania specie, as for example *L.(V)brasiliensis* or any other Leishmania specie present in the first-generation immunotherapeutic agent;

F) isolating seven protein fractions in 8 Molar urea, 0.025 Molar Tris pH 8.3, separated using stepwise elution with 0.05–0.3 Molar NaCl;

G) dialysis vs distilled water and lyophylization of protein fractions;

H) dissolving the protein fractions in phosphate buffered saline;

I) determining protein content of the fractions by the method of Lowry (Lowry, to O. et al, 1951*, J Biol. Chem.*, Vol. 193, pp. 265–275);

J) sonicating each protein fraction in phosphate buffered saline for 5 minutes at 4° C. in a Sonifier Cell Disrupter (Model WI 85, Heath-Systems-Ultrasonic, Inc., Plainview, N.Y.) at the microtip limit of the output control at 50W;

K) passing each fraction through 0.20 $\mu$m Millipore® filters; and

L) forming a second-generation immunizing inoculum comprising one or more of said protein fractions by resuspending the one or more fractions in phosphate buffered saline containing alumina.

EXAMPLE 5

Treatment of Psoriasis With a First-generation Polyvalent Immunotherapeutic Agent Containing *L.(L)amazonensis, L.(L)venezuelensis, L.(L) brasiliensis*, and *L.(L)chagasi*

TABLE 2

Age groups in the study population.

| Age groups | Patients | % |
|---|---|---|
| [0–5] | 8 | 0.29 |
| [6–12] | 65 | 2.35 |
| [13–18] | 90 | 3.25 |
| [19–25] | 268 | 9.68 |
| [26–40] | 997 | 35.99 |
| [41–65] | 1196 | 43.18 |
| >65 | 146 | 5.27 |
| Total | 2770 | 100 |

The majority of patients (79.17%) were between 26–65 years of age with average age of 42.56±26.11 years and a range between 1 and 88 years of age.

TABLE 3

Characteristics of the study population.

| | PATIENTS | AGE | TIME (YEARS) WITH PSORIASIS | PATIENTS HAVING RELATIVES WITH PSORIASIS |
|---|---|---|---|---|
| Males | 1545 (55.8%) | 42.1 ± 14.3 | 11.2 ± 9.6 | 500 (32.3%) |
| Females | 1225 (44.2%) | 38.6 ± 15.3 | 12.0 ± 10.0 | 472 (38.5%) |
| Age ≤25 | 431 (15.6%) | 18.7 ± 5.5 | 6.1 ± 4.8 | 172 (39.9%) |
| Age ≥26 | 2339 (84.4%) | 44.6 ± 12.4 | 12.6 ± 10.2 | 800 (34.2%) |
| Total | 2770 | 40.6 ± 14.9 | 11.6 ± 9.8 | 972 (35.0%) |

35% had parents with psoriasis and the evolution time of the disease was 11.6±9.8 years, similar in males and females, with a range between 2 and 46 years.

TABLE 4

Clinical types of Psoriasis in the study population.

| | PLAQUE | GUTATA | PLAQUE + GUTATA | PALM PLANT-AR | ERYTHRO-DERMIA | INVERSE | PLAQUE + ARTHRITIS | NAILS |
|---|---|---|---|---|---|---|---|---|
| Male | 1229 (56.1%) | 67 (48.9%) | 78 (56.9%) | 37 (39.4%) | 36 (72.0%) | 14 (58.3%) | 53 (55.2%) | 29 (72.5%) |
| Female | 963 (43.9%) | 70 (51.1%) | 59 (43.1%) | 57 (60.6%) | 14 (28.0%) | 10 (41.7%) | 43 (44.8%) | 11 (27.5%) |
| Age ≤25 | 320 (14.6%) | 33 (24.1%) | 24 (17.5%) | 19 (20.2%) | 10 (20%) | 3 (12.5%) | 8 (8.3%) | 5 (12.5%) |
| Age ≥26 | 1872 (85.4%) | 104 (75.9%) | 113 (82.5%) | 75 (79.8%) | 40 (80%) | 21 (87.5%) | 88 (91.7%) | 35 (87.5%) |
| Total | 2192 (79.1%) | 137 (10.1%) | 137 (10.1%) | 94 (0.3%) | 50 (1.8%) | 24 (0.8%) | 96 (3.4%) | 40 (0.3%) |

92.6% had the clinical form of plaque psoriasis distributed in its pure form (79.1%) or associated with guttata (10.1%) or arthritis (3.4%); 10.1% had the Gutata pure form; 0.3% had the palmar and plantar form, 1.8% had Erythrodermia and 3.4% had psoriatic arthritis.

Ninety six % of patients responded to treatment with a decrease in PASI values greater than 10%, and only 4% responded with a decrease in PASI values less than 10% from the initial PASI value before treatment. Twenty eight % had 100% remission of lesions, their disease disappeared completely, similar in males and females. Overall 74% had between 70–100% remission of lesions and 21% from 10–69% remission as compared with initial PASI values. 17.4% of volunteers quit treatment after 1–2 doses of immunotheraputic agent (see below)

TABLE 5

Study population and response to vaccination in psoriatic patients distributed by gender and age.

| | PATIENTS | PASI[1] BEFORE IMMUNOTH ERAPEUTIC AGENT | REDUCTION OF PASI[1] AFTER VACCINATION[2] | | | | | QUIT |
|---|---|---|---|---|---|---|---|---|
| | | | 100% | 99–70% | 69–40% | 39–10% | <10% | QUIT |
| Males | 1545 | 18.5±16.9 | 323 (49.8%) | 600 (57.0%) | 185 (56.7%) | 105 (61.8%) | 55 (59.8%) | 272 (56.5%) |
| Females | 1225 | 13.7±14.9 | 325 (50.2%) | 453 (43.0%) | 141 (43.3%) | 65 (38.2%) | 37 (40.2%) | 209 (43.5%) |
| Age ≤25 | 431 | 13.0±14.7 | 131 (20.2%) | 150 (14.2%) | 50 (15.3%) | 24 (14.1%) | 12 (13.0%) | 69 (14.3%) |
| Age ≥26 | 2339 | 17.0±16.4 | 517 (79.8%) | 903 (85.8%) | 276 (84.7%) | 146 (85.9%) | 80 (87.0%) | 412 (85.7%) |
| Total | 2770 | 16.4±16.2 | 648 (28.0%) | 1053 (46%) | 326 (14.0%) | 170 (7%) | 92 (4%) | 481 (17.4%) |

[1]PASI = Psoriasis area and severity index
[2]Eight years of follow-up

TABLE 6

Comparison of immunotherapeutic agent doses in each clinical remission group.
IMMUNOTHERAPEUTIC AGENT DOSES FOR REDUCTION OF PASI AFTER VACCINATION[1]

|  |  | 100% | 99–70% | 69–40% | 39–10% | <10% | QUIT |
|---|---|---|---|---|---|---|---|
| Males | 1545 | 7.7 ± 6.5 | 11.3 ± 10.8 | 9.2 ± 10.2 | 5.9 ± 4.5 | 6.1 ± 4.8 | 1.6 ± 1.1 |
| Females | 1225 | 7.5 ± 5.6 | 10.6 ± 10.0 | 8.8 ± 8.7 | 6.0 ± 4.6 | 5.9 ± 5.0 | 1.5 ± 1.1 |
| Age ≦ 25 | 431 | 6.5 ± 4.2 | 10.6 ± 10.0 | 8.2 ± 8.4 | 6.1 ± 6.1 | 6.5 ± 4.6 | 1.4 ± 0.6 |
| Age ≧ 26 | 2339 | 7.8 ± 6.4 | 11.1 ± 10.0 | 9.2 ± 9.8 | 5.9 ± 4.2 | 5.9 ± 5.0 | 1.7 ± 1.4 |
| Total | 2770 | 7.6 ± 6.0 | 11.0 ± 10.0 | 9.0 ± 9.6 | 6.0 ± 4.5 | 6.0 ± 4.9 | 1.7 ± 1.4 |

[1]Subjects' conditions were followed for eight years.

7.6±6.0 doses of immunotherapeutic agent were needed for 100% remission of psoriasis. The amount of doses in the groups with 70–90% and 40–69% remission were somewhat higher, reaching values of 11.0±10.0 and 9.0±9.6 respectively, which suggests that clinical remission depends mainly on the immunological response of the volunteer. The patient able to respond to the immunotherapeutic agent antigens is committed to do so since the beginning of treatment. The patient without response stays so, in spite of a higher number of immunotherapeutic agent doses.

Minor side effects were observed at the site of inoculation in less than half of the patients with psoriasis, without difference due to gender or age. All of these disappeared within a few days. Results of the laboratory analysis of samples from 55 psoriasis patients who received 21.4±13.1 doses of first-generation immunotherapeutic agent are shown in Table 9. All values were found to be within normal ranges.

TABLE 7

Appearance of relapses after clinical remission of Psoriasis.
APPEARANCE OF RELAPSES AFTER REMISSION IN 100% REMISSION GROUP

| Relapses | Initial PASI | Doses for 100% remission | Time[1] for 100% remission | PASI at relapse | Time[1] from remission to relapse | PASI at new remission | Doses for new remission | Time[1] for new remission | % New remissions after relapse |
|---|---|---|---|---|---|---|---|---|---|
| 188/648 (28.9%) | 21.0 ± 17.8 | 7.6 ± 6.0 | 7.0 ± 5.4 | 7.7 ± 10.1 | 15.4 ± 20.6 | 2.8 ± 3.3 | 7.1 ± 6.8 | 5.8 ± 4.9 | 161/188 (85.6%) |

[1]months

From the 648 patients with total remission of lesions 188 (28.9%) volunteers had relapses of the disease after 15.4±20.6 months. PASI values at the time of relapse were ⅓ of the initial PASI value before treatment. The PASI at the new Clinical remission was considerable lower than the PASI at the time of relapse. The new remission occurred with 7.1±6.8 doses of immunotherapeutic agent after 5.8±4.9 weeks, a period of time lower than the time period observed in the first treatment cycle for Clinical remission of lesions. In this relapsing group 85.6% of patients had again remission of lesions after 6–7 doses of immunotherapeutic agent.

TABLE 8

Side effects after vaccination.

| SIGNS AT THE SITE OF INOCULATION | | | | SYSTEMIC | |
|---|---|---|---|---|---|
| Pain | Heat | Redness | Nodule | SYMPTOMS | NONE |
| 989 (43.2%) | 484 (21.1%) | 327 (14.3%) | 535 (23.4%) | 588 (25.7%) | 1233 (53.9%) |

TABLE 9

Laboratory analysis in 55 psoriasis patients with 21.4 ± 13.1 doses of first-generation immunotherapeutic agent.

| | |
|---|---|
| White blood cell count/ul | 6003 ± 4165 |
| % Neutrophiles | 53.1 ± 13.3 |
| % Lymphocytes | 29.3 ± 13.3 |
| % Monocytes | 5.8 ± 3.8 |
| % Eosynophiles | 2.9 ± 2.3 |
| % Basophiles | 0.7 ± 0.6 |
| Red blood cell count × $10^6$/ul | 4.7 ± 0.6 |
| Hemoglobin g/dl | 13.3 ± 1.9 |
| Hematocrit (%) | 42.0 ± 5.9 |
| VCM (fl) | 91.6 ± 7.7 |
| MCH (pg) | 29.2 ± 3.2 |
| MCHC (g/dl) | 31.9 ± 1.0 |
| RDW-SD (fl) | 20.1 ± 14.9 |
| Platelets × $10^6$/ul | 250.3 ± 84.2 |
| UREA (mg/dl) | 19.7 ± 8.5 |
| CREATININE (mg/dl) | 0.9 ± 0.2 |
| URIC ACID (mg/dl) | 5.6 ± 1.6 |
| BLOOD SUGAR (mg/dl) | 89.8 ± 15.1 |
| TOTAL PROTEIN (g/dl) | 7.2 ± 0.8 |
| ALBUMINE (g/dl) | 3.8 ± 0.9 |
| GLOBULINES (g/dl) | 3.3 ± 0.8 |
| TRIGLICERIDES (mg/dl) | 161.0 ± 107.1 |
| LOW DENSITY LIPOPROTEINS (mg/dl) | 102.8 ± 44.5 |
| VERY LOW DENSITY LIPOPROTEINS (mg/dl) | 35.0 ± 23.3 |

TABLE 9-continued

Laboratory analysis in 55 psoriasis patients with 21.4 ± 13.1 doses of first-generation immunotherapeutic agent.

| | |
|---|---|
| LACTIC ACID DEHYDROGENASE (mg/dl) | 36.1 ± 13.2 |
| PROTROMBIN TIME | 11.7 ± 1.3 |
| TROMBOPLASTIN PARTIAL TIME | 29.5 ± 6.5 |
| OXALOACETIC TRANSAMINASE (u/l) | 29.0 ± 14.1 |
| PYRUVIC TRANSAMINASE (u/l) | 26.1 ± 15.1 |
| SODIUM (mg/dl) | 144.9 ± 2.1 |
| POTASSIUM (mg/dl) | 4.2 ± 0.3 |
| CHLORINE (meq/l) | 105.3 ± 2.6 |
| CALCIUM (mg/dl) | 8.7 ± 0.3 |
| PHOSPHORUS (mg/dl) | 2.9 ± 0.4 |

EXAMPLE 6

Trial of First-generation Monovalent Immunotherapeutic Agent

TABLE 10

Follow-up of a single blind trial after injection of psoriasis patients with one of four Leishmania species present in the first-generation immunotherapeutic agent.

| LEISHMANIA SPECIE | PASI BEFORE TREATMENT | IMMUNO-THERAPEUTIC AGENT DOSES | PASI AFTER TREATMENT | % PASI REDUCTION |
|---|---|---|---|---|
| L.(L) amazonensis | 6.4 | 3 | 1.4 | 78.1 |
| L.(L) amazonensis | 3.8 | 6 | 1.7 | 55.3 |
| L.(L) amazonensis | 3.6 | 3 | 1.4 | 61.1 |
| L.(L) amazonensis | 9.4 | 5 | 1.3 | 86.2 |
| L.(L) amazonensis | 2.3 | 3 | 0 | 100.0 |
| L.(V) brasiliensis | 36 | 2 | 15.4 | 57.2 |
| L.(V) brasiliensis | 11.9 | 2 | 1.8 | 84.9 |
| L.(V) brasiliensis | 13.9 | 5 | 6.4 | 54.0 |
| L.(V) brasiliensis | 5.8 | 4 | 1.9 | 67.2 |
| L.(L) chagasi | 2.8 | 5 | 0 | 100.0 |
| L.(L) chagasi | 52.2 | 3 | 0 | 100.0 |
| L.(L) chagasi | 10 | 3 | 4.5 | 55.0 |
| L.(L) venezuelensis | 15.6 | 3 | 5.3 | 66.0 |

Immunotherapeutic agents were also prepared using individual species of Leishmania from the first generation Immunotherapeutic agent and were subsequently tested for ability to induce Clinical remission of psoriasis lesions. The results in Table 15 clearly demonstrated that it is not necessary to prepare a mixture of four Leishmania species in the first generation Immunotherapeutic agent to obtain clinical remission of lesions in psoriasis patients. One Leishmania species is as effective as the mixture of four species used in the polyvalent immunotherapeutic agent to induce lower PASI values up to 100% after treatment. Thus, in every leishmania extract, there is a factor that inhibits the inflammation associated with psoriasis.

EXAMPLE 7

Formulation and Administration

The compounds of the invention are useful for various purposes, both therapeutic and non-therapeutic. Therapeutic application of the new compounds and compositions containing them can be contemplated to be accomplished by any suitable therapeutic method and technique presently or prospectively known to those skilled in the art. Further, the compounds of the invention have utility as starting materials or intermediates for the preparation of other useful compounds and compositions.

The dosage administered to a host in the above indications will be dependent upon the identity of the infection, the type of host involved, including the host's age, weight, and health, the existence and nature of concurrent treatments, if any, the frequency of treatment, and the therapeutic ratio.

The compounds of the subject invention can be formulated according to known methods for the preparation of pharmaceutical compositions. Formulations are described in detail in a number of sources which are well known and readily available to those skilled in the art. For example, Remington's Pharmaceutical Science by E. W. Martin describes formulations that can be used in connection with the subject invention. In general, the compositions of the subject invention will be formulated such that an effective amount of the bioactive compound(s) is (are) combined with a suitable carrier in order to facilitate effective administration of the composition.

EXAMPLE 8

Chromatographic Separation of Protein Fractions from Leishmania Species and Blastogenic Assay with Human Peripheral Blood Mononuclear Cells Seven fractions were separated from the particulate Leishmania chagasi extract (PP75), the first component of the first-generation immunotherapeutic agent, after treatment of the respective amastigote parasites with TLCK and extraction with NP-40 as mentioned previously.

The fractions were tested in a blastogenic assay with peripheral blood mononuclear cells from psoriatic patients before and after vaccination according to methods routinely used in the art. For this example, 100 $\mu$l aliquots (triplicates) of each of the fractions dissolved in RPMI-1640 were pre-incubated in flat bottom microtiter plates (Falcon Plastics) with $2\times10^5$ peripheral blood mononuclear cells, separated in HISTOPAQUE (Sigma) and resuspended in 100 $\mu$l of RPMI-1640 containing 20% heat inactivated fetal bovine serum under methods routine in the art. Concanavalin A was used as positive control of lymphocyte stimulation. 48 hours latter, 0.2 $\mu$Ci/well of $^3$H-Thymidine was added in 10 $\mu$l aliquots and the samples were incubated for 18 additional hours. The cells were harvested on filter paper (Reeve Angel) using an automatic cell harvester (MASHII). The dried paper discs were placed in minivials with 2.5 ml Aquasol (NEN) and counted for 1 min. in a Packard Tri-Carb scintillation counter Model 3385. The stimulation index (S.I.) was calculated for each sample by dividing the experimental counts per minute (c.p.m.) by the control c.p.m. (cultures with fractions or mitogens/control cultures in culture medium alone). The results are illustrated in Tables 11–14 below.

TABLE 11

Peripheral blood mononuclear cells blastogenesis with fractions from L(L). chagasi (PP75) before and after vaccination.

| DEAE Sephadex | ug protein/ well | BEFORE VACCINATION n = 3 | | CURED AFTER VACCINATION n = 5 | |
|---|---|---|---|---|---|
| | | cpm/well X ± SD | S.I. X ± SD | cpm/well X ± SD | S.I. X ± SD |
| Fraction 1 | 20 | 823 ± 215 | 1.90 ± 0.22 | 2044 ± 1825 | 3.22 ± 286 |
| No NaCl | 10 | 1297 ± 835 | 2.81 ± 1.5 | 1442 ± 1425 | 2.59 ± 276 |
| | 5 | 1587 ± 1429 | 3.40 ± 2.79 | 1424 ± 1150 | 2.44 ± 217 |
| | 2.5 | 627 ± 282 | 1.40 ± 0.41 | 1366 ± 951 | 2.27 ± 1.66 |
| Fraction 2 | 20 | 908 ± 103 | 2.22 ± 0.79 | 2643 ± 1798 | 4.36 ± 2.96 |
| 0.05 M Nacl | 10 | 821 ± 660 | 1.87 ± 1.1 | 1880 ± 1571 | 3.13 ± 2.83 |
| | 5 | 761 ± 324 | 1.73 ± 0.49 | 1627 ± 1137 | 2.75 ± 2.05 |
| | 2.5 | 532 ± 347 | 1.19 ± 0.63 | 1129 ± 900 | 1.94 ± 1.7 |
| Fraction 3 | 20 | 933 ± 728 | 2.03 ± 1.37 | 1735 ± 1764 | 3.03 ± 3.4 |
| 0.1 M NaCl | 10 | 941 ± 552 | 2.08 ± 1.77 | 1368 ± 1528 | 2.51 ± 2.94 |
| | 5 | 706 ± 376 | 1.57 ± 0.61 | 1360 ± 1681 | 2.45 ± 3.23 |
| | 2.5 | 717 ± 632 | 1.57 ± 1.21 | 1174 ± 1382 | 2.09 ± 2.66 |
| Fraction 4 | 20 | 674 ± 405 | 1.54 ± 0.74 | 2514 ± 1552 | 4.25 ± 2.73 |
| 0.15 M NaCl | 10 | 600 ± 305 | 1.38 ± 0.55 | 1541 ± 1548 | 2.74 ± 3.0 |
| | 5 | 767 ± 275 | 1.87 ± 0.84 | 1330 ± 1520 | 2.36 ± 2.93 |
| | 2.5 | 940 ± 346 | 2.35 ± 1.29 | 1216 ± 1225 | 2.16 ± 2.37 |
| Fraction 5 | 20 | 549 ± 197 | 1.24 ± 0.21 | 1411 ± 1629 | 2.52 ± 3.14 |
| 0.2 M NaCl | 10 | 472 ± 181 | 1.48 ± 0.58 | 1398 ± 1562 | 2.49 ± 3.01 |
| | 5 | 470 ± 205 | 1.06 ± 0.31 | 1095 ± 1023 | 1.94 ± 1.98 |
| | 2.5 | 353 ± 112 | 0.87 ± 0.03 | 1059 ± 907 | 1.86 ± 1.76 |
| Fraction 6 | 20 | 726 ± 126 | 1.70 ± 0.12 | 1448 ± 1127 | 2.52 ± 2.17 |
| 0.25 M NaCl | 10 | 558 ± 225 | 1.26 ± 0.31 | 1354 ± 818 | 2.46 ± 1.77 |
| | 5 | 778 ± 456 | 1.71 ± 0.78 | 1280 ± 752 | 2.28 ± 1.52 |
| | 2.5 | 688 ± 574 | 1.52 ± 1.09 | 927 ± 710 | 1.61 ± 1.36 |
| Fraction 7 | 20 | 694 ± 325 | 1.54 ± 0.48 | 1180 ± 747 | 1.91 ± 1.09 |
| 0.3 M NaCl | 10 | 676 ± 154 | 1.56 ± 0.10 | 1608 ± 1107 | 2.96 ± 2.27 |
| | 5 | 604 ± 217 | 1.39 ± 0.31 | 1325 ± 601 | 2.40 ± 1.32 |
| | 2.5 | 580 ± 315 | 1.28 ± 0.52 | 1466 ± 810 | 2.75 ± 1.89 |
| Concanavalin A | 10 | 8452 ± 7470 | 23.12 ± 24.89 | 7988 ± 2805 | 13.58 ± 4.31 |
| | 5 | 22479 ± 10642 | 55.05 ± 29.29 | 28011 ± 8183 | 52.67 ± 22.89 |
| Amastigote Parasites | $4 \times 10^6$ | 795 ± 209 | 1.85 ± 0.32 | 2099 ± 1454 | 3.40 ± 2.02 |
| | $2 \times 10^6$ | 741 ± 307 | 1.68 ± 0.45 | 1725 ± 1028 | 2.75 ± 0.99 |
| Culture medium | | 323 ± 79 | 1.0 ± 0.2 | 987 ± 226 | 1.0 ± 0.3 |

The group of patients before vaccination had S.I.>1.0. These values increased markedly after vaccination. Results of the statistical analysis of both groups are as follows:

| Parameter | Before vaccination | After vaccination |
|---|---|---|
| Mean | 1.697143 | 2.571072 |
| # points | 28 | 28 |
| Std deviation | .5298834 | .6259645 |
| Std error | .1001386 | .1182962 |
| Minimum | .87 | 1.61 |
| Maximum | 3.4 | 4.36 |

Paired t test:

Mean difference=−0.8739286 (Mean of paired differences)

95% confidence interval of the difference: −1.150029 to −0.5978283

Two-tailed p value is <0.0001—extremely significant

These results demonstrate that, after vaccination of psoriatic patients with any of the fractions of the L.(L)chagasi extract, lymphocytes are significantly stimulated. Higher stimulation index was observed with fractions 3 and 4 as well as live amastigotes.

Seven fractions were separated from the particulate L(V) brasiliensis extract (PMH27), a second component of the first-generation immunotherapeutic agent, after treatment of the respective amastigote parasites with TLCK and extraction with NP-40 as mentioned previously.

TABLE 12

Peripheral blood mononuclear cells blastogenesis with fractions from
L.(V)brasiliensis (PMH27) before and after vaccination.

| DEAE Sephadex | ug protein/well | BEFORE VACCINATION N = 3, S.I. < 1.0 | | BEFORE VACCINATION N = 2, S.I. > 1.0 | | AFTER VACCINATION CURED, N = 3 | |
|---|---|---|---|---|---|---|---|
| | | cpm/well X ± SD | S.I. X ± SD | cpm/well X ± SD | S.I. X ± SD | cpm/well X ± SD | S.I. X ± SD |
| Fraction 1 No NaCl | 20.00 | 379 ± 23 | 0.85 ± 0.35 | 812 ± 416 | 1.74 ± 0.47 | 1074 ± 509 | 1.98 ± 0.86 |
| | 10.00 | 391 ± 65 | 0.84 ± 0.17 | 1423 ± 1173 | 2.99 ± 1.78 | 1945 ± 2481 | 3.51 ± 4.41 |
| | 5.00 | 491 ± 115 | 1.10 ± 0.46 | 1391 ± 1120 | 3.04 ± 1.8 | 683 ± 224 | 1.26 ± 0.36 |
| | 2.50 | 376 ± 105 | 0.80 ± 0.18 | 879 ± 137 | 2.06 ± 0.59 | 650 ± 240 | 1.19 ± 0.39 |
| Fraction 2 0.05 M NaCl | 20.00 | 902 ± 775 | 1.76 ± 1.28 | 2686 ± 2098 | 5.88 ± 3.4 | 2157 ± 267 | 4.01 ± 0.48 |
| | 10.00 | 709 ± 555 | 1.39 ± 0.89 | 1971 ± 399 | 5.05 ± 3.13 | 1428 ± 351 | 2.65 ± 0.61 |
| | 5.00 | 1385 ± 639 | 3.12 ± 1.65 | 1690 ± 203 | 4.30 ± 2.51 | 1911 ± 533 | 3.56 ± 1.01 |
| | 2.50 | 1117 ± 1004 | 2.19 ± 1.67 | 2887 ± 716 | 6.59 ± 1.28 | 1661 ± 1225 | 3.01 ± 2.15 |
| Fraction 3 0.1 M NaCl | 20.00 | 263 ± 21 | 0.58 ± 0.19 | 1028 ± 163 | 2.59 ± 1.46 | 2237 ± 1002 | 4.13 ± 1.75 |
| | 10.00 | 231 ± 65 | 0.48 ± 0.07 | 928 ± 314 | 2.06 ± 0.25 | 1633 ± 594 | 3.01 ± 1.0 |
| | 5.00 | 207 ± 44 | 0.44 ± 0.05 | 787 ± 365 | 1.74 ± 0.47 | 1479 ± 983 | 2.74 ± 1.76 |
| | 2.50 | 200 ± 41 | 0.42 ± 0.04 | 618 ± 252 | 1.40 ± 0.41 | 1140 ± 767 | 2.09 ± 1.36 |
| Fraction 4 0.15 M NaCl | 20.00 | 251 ± 51 | 0.58 ± 0.30 | 1046 ± 335 | 2.41 ± 0.7 | 946 ± 513 | 2.75 ± 0.92 |
| | 10.00 | 260 ± 87 | 0.54 ± 0.19 | 1272 ± 767 | 2.74 ± 1.04 | 1118 ± 349 | 2.06 ± 0.56 |
| | 5.00 | 279 ± 67 | 0.59 ± 0.08 | 1442 ± 821 | 3.27 ± 1.42 | 915 ± 362 | 1.68 ± 0.6 |
| | 2.50 | 233 ± 37 | 0.50 ± 0.13 | 1335 ± 783 | 2.83 ± 0.96 | 930 ± 414 | 1.71 ± 0.71 |
| Fraction 5 0.2 M NaCl | 20.00 | 232 ± 59 | 0.49 ± 0.05 | 669 ± 157 | 1.54 ± 0.39 | 1306 ± 365 | 2.42 ± 0.62 |
| | 10.00 | 275 ± 37 | 0.62 ± 0.25 | 577 ± 170 | 1.29 ± 0.12 | 911 ± 196 | 1.69 ± 0.33 |
| | 5.00 | 252 ± 64 | 0.54 ± 0.11 | 660 ± 228 | 1.45 ± 0.1 | 753 ± 240 | 1.38 ± 0.38 |
| | 2.50 | 285 ± 135 | 0.58 ± 0.16 | 704 ± 94 | 1.69 ± 0.65 | 822 ± 323 | 1.51 ± 0.53 |
| Fraction 6 0.25 M NaCl | 20.00 | 233 ± 84 | 0.48 ± 0.10 | 873 ± 566 | 1.81 ± 0.76 | 909 ± 123 | 1.68 ± 0.17 |
| | 10.00 | 372 ± 215 | 0.74 ± 0.3 | 895 ± 705 | 1.89 ± 1.08 | 1043 ± 406 | 1.97 ± 0.88 |
| | 5.00 | 436 ± 258 | 0.87 ± 0.37 | 1053 ± 427 | 2.54 ± 1.24 | 971 ± 201 | 1.82 ± 0.48 |
| | 2.50 | 310 ± 76 | 0.66 ± 0.14 | 1308 ± 489 | 3.24 ± 1.82 | 773 ± 206 | 1.43 ± 0.32 |
| Fraction 7 0.3 M NaCl | 20.00 | 1004 ± 881 | 2.03 ± 1.42 | 1406 ± 277 | 3.26 ± 0.8 | 1413 ± 638 | 2.60 ± 1.08 |
| | 10.00 | 2114 ± 1366 | 4.14 ± 1.92 | 2545 ± 1170 | 5.52 ± 1.16 | 1955 ± 472 | 3.62 ± 0.75 |
| | 5.00 | 2295 ± 2915 | 4.19 ± 1.03 | 2549 ± 1291 | 5.71 ± 2.02 | 931 ± 179 | 1.74 ± 0.41 |
| | 2.50 | 349 ± 206 | 0.70 ± 0.28 | 1479 ± 1503 | 2.99 ± 2.42 | 558 ± 186 | 1.02 ± 0.3 |
| Concanavalin A | 10.00 | 17443 ± 9651 | 41.98 ± 32.89 | 7180 ± 2557 | 19.31 ± 15.19 | 20051 ± 12578 | 37.29 ± 22.55 |
| | 5.00 | 30323 ± 2242 | 67.32 ± 21.79 | 14665 ± 12253 | 31.21 ± 19.01 | 33798 ± 4946 | 62.89 ± 8.16 |
| Amastigote parasites | $4 \times 10^6$ | 1035 ± 526 | 2.19 ± 0.87 | 2327 ± 974 | 5.17 ± 1.23 | 5128 ± 826 | 9.52 ± 1.21 |
| | $2 \times 10^6$ | 395 ± 147 | 1 ± 0.05 | 2427 ± 1968 | 4.37 ± 3.52 | 520 ± 33 | 0.90 ± 0.5 |
| Culture medium | | 390 ± 114 | 1.0 ± 0 | 557 ± 49 | 1.0 ± 0.3 | 580 ± 0 | 1.0 ± 0 |

In Table 12, two groups of patients were evident before vaccination, specifically, one group with S.I.<1.0 and another group with S.I. >1.0. The group of patients cured after vaccination had markedly increased values when compared with either of these groups before vaccination. Results of the statistical analysis are as follows:

| | Group with S.I. <1.0 | |
|---|---|---|
| Parameter | Before vaccination | After vaccination |
| Mean | 1.150714 | 2.257857 |
| # points | 28 | 28 |
| Std deviation | 1.062052 | .8876538 |
| Std error | .200709 | .1677508 |
| Minimum | .42 | 1.02 |
| Maximum | 4.19 | 4.13 |

Paired t test:

Mean difference=−1.107143 (Mean of paired differences)

95% confidence interval of the difference: −1.534381 to −0.6799043

Two-tailed p value is <0.0001—extremely significant

| | Group with S.I. >1.0 | |
|---|---|---|
| Parameter | Before vaccination | After vaccination |
| Mean | 2.986429 | 2.257857 |
| # points | 28 | 28 |
| Std deviation | 1.504479 | .8876538 |
| Std error | .2843199 | .1677508 |
| Minimum | 1.29 | 1.02 |
| Maximum | 6.59 | 4.13 |

Unpaired t test:

Mean difference=−0.7285719 (Mean of B minus mean of A)

95% confidence interval of the difference: −1.3904 to −6.674413E-02

Two-tailed p value is <0.0316—significant

These results demonstrate that lymphocytes from both of the pre-vaccination groups are significantly stimulated by vaccination with any of the fractions of the L.(V)brasiliensis extract. Higher stimulation index was observed with fractions 3 and 4 as well as live amastigotes.

Six fractions were separated from the particulate L.(L) venezuelensis extract (PMH16), the third component of the first-generation immunotherapeutic agent, after treatment of the respective amastigote parasites with TLCK and extraction with NP-40 as mentioned previously.

TABLE 13

Peripheral blood mononuclear cells blastogenesis with fractions from
L.(V)venezuelensis (PMH16) before and after vaccination.

| DEAE Sephadex | ug protein/ well | BEFORE VACCINATION n = 5, S.I. < 1.0 | | BEFORE VACCINATION n = 2, S.I. > 1.0 | | CURED AFTER VACCINATION n = 2 | |
|---|---|---|---|---|---|---|---|
| | | cpm/well X ± SD | S.I. X ± SD | cpm/well X ± SD | S.I. X ± SD | cpm/well X ± SD | S.I. X ± SD |
| Fraction 1 | 20.00 | 1617 ± 1622 | 1.95 ± 1.51 | 480 ± 92 | 0.89 ± 0.3 | 826 ± 104 | 1.78 ± 0.42 |
| No NaCl | 10.00 | 1455 ± 1241 | 1.82 ± 1.03 | 737 ± 57 | 1.36 ± 0.72 | 518 ± 74 | 1.11 ± 0.62 |
| | 5.00 | 1222 ± 905 | 1.57 ± 0.66 | 488 ± 75 | 0.90 ± 0.43 | 551 ± 42 | 1.1 ± 0.63 |
| | 2.50 | 1376 ± 1147 | 1.73 ± 0.93 | 468 ± 63 | 0.87 ± 0.27 | 377 ± 27 | 0.812 ± 0.3 |
| Fraction 2 | 20.00 | 1579 ± 1259 | 1.77 ± 1.39 | 1997 ± 1965 | 1.86 ± 1.05 | 2201 ± 419 | 3.52 ± 0.82 |
| 0.05 M NaCl | 10.00 | 1371 ± 476 | 1.65 ± 0.93 | 2163 ± 489 | 2.65 ± 102 | 1840 ± 895 | 2.41 ± 1.89 |
| | 5.00 | 1003 ± 455 | 1.11 ± 0.48 | 1521 ± 1235 | 1.52 ± 0.46 | 1238 ± 1093 | 1.65 ± 0.97 |
| | 2.50 | 785 ± 164 | 0.87 ± 0.19 | 1398 ± 1309 | 1.33 ± 0.65 | 1259 ± 1256 | 1.66 ± 1.23 |
| Fraction 3 | 20.00 | 896 ± 358 | 0.98 ± 0.36 | 1859 ± 2160 | 1.61 ± 1.41 | 3681 ± 170 | 6.08 ± 2.25 |
| 0.1 M NaCl | 10.00 | 948 ± 594 | 1.02 ± 0.53 | 4858 ± 6397 | 3.92 ± 4.67 | 4178 ± 1306 | 7.41 ± 5.06 |
| | 5.00 | 689 ± 268 | 0.77 ± 0.35 | 1299 ± 1182 | 1.25 ± 0.56 | 3802 ± 1792 | 6.96 ± 5.61 |
| | 2.50 | 707 ± 302 | 0.77 ± 0.29 | 1760 ± 1967 | 1.55 ± 1.23 | 2775 ± 276 | 4.53 ± 1.45 |
| Fraction 4 | 20.00 | 848 ± 401 | 0.89 ± 0.25 | 1859 ± 1316 | 1.93 ± 0.3 | 2797 ± 1204 | 4.24 ± 0.08 |
| 0.15 M NaCl | 10.00 | 886 ± 810 | 0.91 ± 0.58 | 1930 ± 95 | 2.49 ± 1.35 | 3734 ± 2376 | 5.40 ± 1.39 |
| | 5.00 | 1105 ± 1103 | 1.07 ± 0.76 | 2024 ± 402 | 2.81 ± 2.08 | 1539 ± 182 | 2.63 ± 1.37 |
| | 2.50 | 826 ± 479 | 0.90 ± 0.49 | 1065 ± 794 | 1.09 ± 0.23 | 1151 ± 442 | 1.76 ± 0.06 |
| Fraction 5 | 20.00 | 1087 ± 618 | 0.91 ± 0.53 | 2416 ± 651 | 2.92 ± 1.0 | 2612 ± 1583 | 4.90 ± 4.44 |
| 0.2 M NaCl | 10.00 | 848 ± 601 | 1.14 ± 1.26 | 1912 ± 427 | 2.34 ± 0.91 | 1648 ± 165 | 2.80 ± 1.41 |
| | 5.00 | 587 ± 230 | 0.65 ± 0.22 | 2092 ± 108 | 2.78 ± 1.75 | 2324 ± 2119 | 4.60 ± 5.13 |
| | 2.50 | 553 ± 186 | 0.62 ± 0.21 | 1434 ± 842 | 1.56 ± 0.1 | 1235 ± 150 | 2.11 ± 1.1 |
| Fraction 6 | 20.00 | 767 ± 15 | 1.14 ± 0.42 | 129 ± 15 | 2.40 ± 0.57 | 1583 ± 640 | 3.41 ± 1.5 |
| 0.25 M NaCl | 10.00 | 515 ± 91 | 0.74 ± 0.16 | 852 ± 22 | 1.58 ± 0.63 | 1659 ± 315 | 3.57 ± 0.95 |
| | 5.00 | 374 ± 31 | 0.55 ± 0.17 | 577 ± 46 | 1.07 ± 0.38 | 592 ± 92 | 1.27 ± 0.47 |
| | 2.50 | 422 ± 17 | 0.62 ± 0.21 | 446 ± 24 | 0.82 ± 0.59 | 491 ± 27 | 1.05 ± 0.35 |
| Concanavalin A | 20.00 | 29329 ± 13560 | 134 ± 237 | 22781 ± 8014 | 23.01 ± 6.19 | 10028 ± 4113 | 21.61 ± 11.25 |
| | 10.00 | 34463 ± 10198 | 40 ± 17 | 48480 ± 8611 | 66.96 ± 48 | 24309 ± 12540 | 52.39 ± 36 |
| | 5.00 | 33799 ± 7901 | 52 ± 31 | 49409 ± 7469 | 63.8 ± 39 | 43290 ± 6532 | 93.29 ± 22.5 |
| | 2.50 | 35113 ± 1040 | 52.28 ± 18 | 42183 ± 10112 | 58.2 ± 19 | 35165 ± 4526 | 75.78 ± 36.5 |
| Amastigote parasites | $4 \times 10^6$ | 1315 ± 404 | 1.55 ± 0.78 | 2933 ± 429 | 3.22 ± 0.11 | 2500 ± 715 | 5.38 ± 1.2 |
| | $2 \times 10^6$ | 1665 ± 452 | 2.36 ± 0.27 | | | 3032 ± 1256 | 6.5 ± 3.4 |
| Culture medium | | 914 ± 237 | 1.0 ± 0.3 | 539 ± 74 | 1.0 ± 0.2 | 464 ± 59 | 1.0 ± 0 |

In Table 13 two groups of patients are evident before vaccination, specifically, one group with S.I.<1.0 and another group with S.I.>1.0. The group of patients cured after vaccination had markedly increased values when compared with either of these pre-vaccination groups. Results of the statistical analysis are as follows:

| | Group with S.I. <1.0 | |
|---|---|---|
| Parameter | Before vaccination | After vaccination |
| Mean | 1.089583 | 3.205 |
| # points | 24 | 24 |
| Std deviation | .4250269 | 1.938181 |
| Std error | 8.675825E-02 | .3956296 |
| Minimum | .55 | .81 |
| Maximum | 1.95 | 7.41 |

Paired t test:

Mean difference=−2.115417 (Mean of paired differences)

95% confidence interval of the difference: −3.008944 to −1.22189

Two-tailed p value is <0.0001—extremely significant

| | Group with S.I. >1.0 | |
|---|---|---|
| Parameter | Before vaccination | After vaccination |
| Mean | 1.814167 | 3.205 |
| # points | 24 | 24 |
| Std deviation | .8092286 | 1.938181 |
| Std error | .165183 | .3956296 |
| Minimum | .83 | .81 |
| Maximum | 3.92 | 7.41 |

Unpaired t test:

Mean difference=−0.7285719 (Mean of B minus mean of A)

95% confidence interval of the difference: −1.3904 to −6.674413E-02

Two-tailed p value is <0.0316—significant

These results demonstrate that lymphocytes from both pre-vaccination groups of patients are significantly stimulated by vaccination with any of the fractions of the L.(L) venezuelensis extract. Higher stimulation index was observed with fractions 3 and 4 as well as live amastigotes.

Seven fractions were separated from the *L.(L) amazonensis* extract (PMH8), the fourth component of the first-generation immunotherapeutic agent, after treatment of the respective amastigote parasites with TLCK and extraction with NP-40 as mentioned previously.

Unpaired t test:
 Mean difference=−0.5710449 (Mean of paired differences)
 95% confidence interval of the difference: 0.3475174 to 0.7945725

TABLE 14

Peripheral blood mononuclear cells blastogenesis with fractions from *L.(L)amazonensis* (PMH8), before and after vaccination.

| DEAE Sephadex | ug protein/ well | BEFORE VACCINATION n = 4, S.I. < 1.0 | | BEFORE VACCINATION n = 4, S.I. > 1.0 | | CURED AFTER VACCINATION n = 4 | |
|---|---|---|---|---|---|---|---|
| | | cpm/well X ± SD | S.I. X ± SD | cpm/well X ± SD | S.I. X ± SD | cpm/well X ± SD | S.I. X ± SD |
| Fraction 1 | 20.00 | 450 ± 22 | 0.84 ± 0.1 | 265 ± 22 | 1 ± 0 | 1525 ± 1374 | 1.48 ± 0.97 |
| No NaCl | 10.00 | 371 ± 19 | 0.70 ± 0.35 | 285 ± 45 | 1.07 ± 0.3 | 1392 ± 1222 | 1.95 ± 1.27 |
| | 5.00 | 392 ± 45 | 0.74 ± 0.14 | 448 ± 17 | 1.69 ± 0.45 | 1211 ± 584 | 1.79 ± 0.46 |
| | 2.50 | 480 ± 62 | 0.9 ± 0.32 | 311 ± 42 | 1.17 ± 0.25 | 1152 ± 733 | 1.67 ± 0.71 |
| Fraction 2 | 20.00 | 735 ± 405 | 0.64 ± 0.16 | 3576 ± 4474 | 3.37 ± 2.57 | 1614 ± 1540 | 2.22 ± 1.66 |
| 0.05 M NaCl | 10.00 | 574 ± 356 | 0.59 ± 0.26 | 1107 ± 1066 | 1.38 ± 0.07 | 1939 ± 1297 | 2.24 ± 1.35 |
| | 5.00 | 580 ± 238 | 0.60 ± 0.13 | 1181 ± 1311 | 1.29 ± 0.47 | 1569 ± 970 | 2.28 ± 1.10 |
| | 2.50 | 522 ± 68 | 0.61 ± 0.25 | 1173 ± 1217 | 1.37 ± 0.27 | 1180 ± 1215 | 1.61 ± 1.3 |
| Fraction 3 | 20.00 | 885 ± 928 | 0.84 ± 0.61 | 1488 ± 1524 | 1.76 ± 0.3 | 1716 ± 1355 | 2.49 ± 1.49 |
| 0.1 M NaCl | 10.00 | 585 ± 164 | 0.59 ± 0.16 | 1582 ± 285 | 3.29 ± 2.71 | 2453 ± 2095 | 3.56 ± 2.31 |
| | 5.00 | 676 ± 284 | 0.75 ± 0.08 | 1073 ± 850 | 1.53 ± 0.35 | 807 ± 423 | 1.21 ± 1.42 |
| | 2.50 | 593 ± 398 | 0.81 ± 0.51 | 1267 ± 1003 | 1.81 ± 0.41 | 807 ± 452 | 1.20 ± 0.45 |
| Fraction 4 | 20.00 | 733 ± 64 | 1.38 ± 0.6 | 349 ± 15 | 1.31 ± 0.4 | 1759 ± 374 | 2.80 ± 0.74 |
| 0.15 M NaCl | 10.00 | 428 ± 26 | 0.84 ± 0.2 | 1293 ± 254 | 4.87 ± 0.52 | 1424 ± 152 | 1.57 ± 0.72 |
| | 5.00 | 297 ± 37 | 0.56 ± 0.15 | 627 ± 90 | 2.36 ± 0.45 | 927 ± 97 | 1.49 ± 0.4 |
| | 2.50 | 374 ± 29 | 0.70 ± 0.14 | 397 ± 26 | 1.49 ± 0.65 | 939 ± 559 | 1.41 ± 0.78 |
| Fraction 5 | 20.00 | 236 ± 16 | 0.44 ± 0.2 | 287 ± 46 | 1.08 ± 0.4 | 442 ± 226 | 0.74 ± 0.5 |
| 0.2 M NaCl | 10.00 | 383 ± 45 | 0.72 ± 0.15 | 231 ± 26 | 0.87 ± 0.22 | 421 ± 127 | 0.67 ± 0.24 |
| | 5.00 | 250 ± 39 | 0.47 ± 0.18 | 236 ± 39 | 0.89 ± 0.16 | 280 ± 55 | 0.44 ± 0.09 |
| | 2.50 | 276 ± 52 | 0.52 ± 0.27 | 302 ± 11 | 1.13 ± 0.45 | 334 ± 43 | 0.54 ± 0.17 |
| Fraction 6 | 20.00 | 251 ± 45 | 0.47 ± 0.14 | 265 ± 93 | 1 ± 0 | 779 ± 354 | 1.05 ± 0.11 |
| 0.25 M NaCl | 10.00 | 284 ± 17 | 0.53 ± 0.21 | 250 ± 42 | 0.94 ± 0.4 | 679 ± 235 | 1.03 ± 0.24 |
| | 5.00 | 262 ± 26 | 0.49 ± 0.11 | 323 ± 196 | 1.22 ± 0.38 | 532 ± 222 | 1.01 ± 0.26 |
| | 2.50 | 264 ± 32 | 0.49 ± 0.12 | 298 ± 29 | 1.12 ± 0.6 | 450 ± 236 | 0.73 ± 0.48 |
| Fraction 7 | 20.00 | 1038 ± 453 | 2.03 ± 0.5 | 522 ± 125 | 1.97 ± 0.5 | 1074 ± 658 | 1.62 ± 0.92 |
| 0.3 M NaCl | 10.00 | 507 ± 144 | 0.96 ± 0.32 | 697 ± 74 | 2.63 ± 0.58 | 668 ± 275 | 1.01 ± 0.27 |
| | 5.00 | 395 ± 61 | 0.74 ± 0.37 | 611 ± 85 | 2.30 ± 0.45 | 898 ± 674 | 1.37 ± 0.9 |
| | 2.50 | 485 ± 56 | 0.91 ± 0.26 | 626 ± 92 | 2.36 ± 0.62 | 732 ± 403 | 1.09 ± 0.52 |
| Concanavalin A | 10 | 33179 ± 9137 | 37.67 ± 16.2 | 25676 ± 13921 | 43.56 ± 22.88 | 18975 ± 10149 | 28.27 ± 11.54 |
| | 5.00 | 31012 ± 12118 | 36.31 ± 7.42 | 39742 ± 3747 | 86.32 ± 75.86 | 17425 ± 7521 | 26.31 ± 8.18 |
| Amastigote Parasites | 4 × 10⁶ | 1775 ± 702 | 2.15 ± 0.67 | 2271 ± 2564 | 2.44 ± 1.0 | 3027 ± 2268 | 4.33 ± 2.69 |
| Culture medium | | 510 ± 89 | 1.00 ± 0.1 | 265 ± 59 | 1.0 ± 0 | 529 ± 67 | 1.0 ± 0 |

In Table 14, two groups of patients are evident before vaccination, specifically, one group with S.I.<1.0 and another group with S.I.>1.0. The group of patients cured after vaccination had markedly increased values when compared with either of these pre-vaccination groups. Results of the statistical analysis are as follows:

| | Group with S.I. <1.0 | |
|---|---|---|
| Parameter | Before vaccination | After vaccination |
| Mean | .7007408 | 1.271786 |
| # points | 27 | 28 |
| Std deviation | .2043736 | .5430509 |
| Std error | .0393317. | .102627 |
| Minimum | .45 | .47 |
| Maximum | 1.39 | 3.15 |

Two-tailed p value is <0.0001—extremely significant

| | Group with S.I. >1.0 | |
|---|---|---|
| Parameter | Before vaccination | After vaccination |
| Mean | 1.726786 | 1.271786 |
| # points | 28 | 28 |
| Std deviation | .9234719 | .5430509 |
| Std error | .1745198 | .102627 |
| Minimum | .88 | .47 |
| Maximum | 4.88 | 3.15 |

Unpaired t test:
 Mean difference=−0.4549999 (Mean of B minus mean of A)
 95% confidence interval of the difference: −0.8608927 to −4.910712E-02
 Two-tailed p value is <0.0287—significant These results demonstrate that lymphocytes from both pre-vaccination groups of patients are significantly stimulated by vaccination with any of the fractions of the *L.(L) amazonensis* extract. Higher stimulation index was observed with fractions 3 and 4 as well as live amastigotes. In summary, each of the blastogenesis experiments demonstrate that vaccination with any of the protein fractions from each of the leishmania species included in the first-generation immunotherapeutic agent, and particularly fractions 3 and 4, results in significant stimulation of lymphocytes. The stimulated lymphocytes produce cytokines that can inhibit the inflammatory response in psoriatic patients, thus inducing clinical remission of the psoriatic lesions.

EXAMPLE 14

Humoral Immunity in Psoriatic Patients

TABLE 15

ELISA in psoriatic patients before and after vaccination.
(O'Daly et al.1994 Acta Tropica 56:265–287)

| Number of Patients | Immunotherapeutic agent Doses | Optical Density 405 nm (Average ± S.D.) | | | |
|---|---|---|---|---|---|
| | | La | Lv | Lb | Lch |
| 36 | 0 | 0.21 ± 0.20 | 0.40 ± 0.18 | 0.37 ± 0.22 | 0.35 ± 0.18 |
| 13 | 1 | 0.12 ± 0.00 | 0.21 ± 0.09 | 0.22 ± 0.10 | 0.19 ± 0.07 |
| 18 | 2 | 0.37 ± 0.27 | 0.35 ± 0.16 | 0.32 ± 0.17 | 0.33 ± 0.14 |
| 17 | 3 | 0.47 ± 0.22 | 0.38 ± 0.15 | 0.41 ± 0.20 | 0.36 ± 0.10 |
| 12 | 4 | 0.41 ± 0.28 | 0.30 ± 0.11 | 0.22 ± 0.09 | 0.26 ± 0.03 |
| 12 | 6 | 0.38 ± 0.27 | 0.34 ± 0.18 | 0.36 ± 0.05 | 0.30 ± 0.01 |
| 16 | Active leishmaniasis | 0.91 ± 0.27 | 0.82 ± 0.21 | 0.77 ± 0.24 | 0.92 ± 0.26 |

La: Leishmania amazonensis ; Lv:L.venezuelensis Lb: L. brasiliensis ; Lch: L. chagasi Sera from psoriasis patients were assayed before and after vaccination with an Enzyme Linked Immunosorbent Assay (ELISA), the results of which are shown in Table 15. No difference in optical density values was observed between pre-vaccination and post-vaccination samples up to clinical remission of lesions after six doses of the first-generation immunotherapeutic agent. The cut-off point for a positive reaction was 0.5 units. The only positive sera belonged to samples from patients with active leishmaniasis. This demonstrates that the first-generation immunotherapeutic agent is not inducing Humoral Immunity or TH2 responses.

EXAMPLE 15

Cellular Immunity in Psoriatic Patients

The results of intradermic reaction assays for cellular immunity are shown in Table 16. The data indicate that the first-generation immunotherapeutic agent is inducing a TH1 response in cured psoriasis patients. Fraction 3 of the *L.(L)chagasi* and *L.(V)brasiliensis* antigenic components of the first-generation immunotherapeutic agent demonstrates the highest immunogenic activity in vivo with the intradermic reaction assay after clinical remission of lesions. Fraction 4 from either of these species also shows a high degree of activity.

EXAMPLE 16

Single Blind Trial with Second-generation Immunotherapeutic Agent Containing Isolated Protein Antigenic Fractions

TABLE 17

Response to vaccination with second-generation immunotherapeutic agent.

| Numbers of patients | Fraction | Numbers of Doses | Initial PASI | Final PASI | % Decrease in Final PASI |
|---|---|---|---|---|---|
| 3 | 1 | 2.0 ± 1.0 | 25.0 ± 13.1 | 10.8 ± 4.6 | 56.8 |
| 7 | 2 | 2.0 ± 1.3 | 24.9 ± 22.4 | 13.1 ± 23.9 | 47.4 |
| 14 | 3 | 2.1 ± 1.1 | 16.1 ± 14.7 | 1.9 ± 2.9 | 88.2 |
| 11 | 4 | 2.3 ± 0.5 | 19.3 ± 15.1 | 2.4 ± 3.8 | 87.6 |
| 8 | 5 | 2.2 ± 0.8 | 28.8 ± 21.3 | 13.5 ± 15.5 | 52.8 |
| 3 | 6 | 2.3 ± 0.6 | 16.7 ± 1.0 | 8.2 ± 6.8 | 50.9 |

The effect of vaccination with the fractions of the second-generation immunotherapeutic agent on PASI values is shown in Table 17. Fractions 3 and 4 show the highest activity for clinical remission of psoriasis. Two doses of immunotherapeutic agent incorporating either of these fractions decrease the PASI by 88% of their initial values in patients before vaccination. These fractions also displayed the highest stimulation indexes in the in vitro blastogenesis experiments and the highest in vivo intradermic reaction (IDR) diameter after vaccination in the patients cured of psoriasis.

EXAMPLE 17

Identification and Characterization of Protein Fractions that Induce Clinical Remission of Psoriatic Lesions Peptide gels were transferred to nitrocellulose papers and analyzed at the ICBR Protein Chemistry CORE Facility at the University of Florida, Gainsville, Fla. HPLC was performed using a Hewlett Packard 1090 HPLC, digestion was performed with Endo-Lys-C, and amino acid analysis was performed using an ABI 494 Protein Sequencer. Amino acid sequence homology was searched using the BLAST program.

TABLE 16

Intradermic reaction to antigenic fractions in patients after clinical remission of psoriasis.
IDR DIAMETER (mm)

| | | CHROMATOGRAPHY FRACTIONS | | | | | | | |
|---|---|---|---|---|---|---|---|---|---|
| Parasite | Patients | 1 | 2 | 3 | 4 | 5 | 6 | 7 | P[1] |
| L.(L)chagasi | 15 | 5.3 ± 3.5 | 8.6 ± 5.8 | 21.7 ± 5.0 | 12.3 ± 5.8 | 11.4 ± 6.2 | 5.8 ± 4.8 | 4.5 ± 3.3 | <0.0001 |
| L.(V)brasiliensis | 20 | 3.4 ± 3.1 | 8.2 ± 6.2 | 14.9 ± 5.5 | 10.8 ± 4.9 | 5.8 ± 4.2 | 3.2 ± 1.9 | 3.0 ± 1.9 | <0.0001 |

[1]Fraction 3 vs other fractions

TABLE 18

Amino acid sequence of peptides.

| Protein fraction | Band | Peptide number | Sequence | Sequence ID | Peptide length | Homology with human proteins |
|---|---|---|---|---|---|---|
| 3 | 82 | 2 | 12 YEDEINK | 1 | 7 | KERATIN TYPE II |
| | | | 16 AQYEDIAQK | 2 | 9 | KERATIN TYPE II |
| | 80 | 3 | 13 EIETYHNLLEGGQEDF | 3 | 16 | KERATIN TYPE I CITOSKELETAL |
| | | | AQYEDAIK | 4 | 9 | KERATIN TYPE II |
| | | | 10 YEDEINK | 1 | 7 | KERATIN TYPE II |
| | 73 | 4 | 10 YEDEINK | 1 | 7 | KERATIN TYPE II |
| | | | 12 AEAESLY | 5 | 7 | — |
| | | | 13 NYSPYYNTIDDL | 6 | 12 | KERATIN TYPE I CITOSKELETAL |
| 4 | 82 | 2 | 4 AEAESLYQSK | 7 | 10 | KERATIN TYPE II |
| | | | 9 ATNAENEFV | 8 | 9 | KERATIN TYPE II |
| | | | 22 XXYSELNRVIQRLRSI | 9 | 16 | KERATIN TYPE II |
| | 80 | 3 | 18 EIETYHNLLEGGQEDF | 3 | 16 | KERATIN TYPE I CITOSKELETAL |
| | | | 9 YEDEINK | 1 | 7 | KERATIN TYPE II |
| | | | 11 AQYEDYAQ | 10 | 8 | KERATIN TYPE II |
| | 73 | 4 | 8 YEDEINNK | 11 | 8 | — |
| | | | 10 KYEDEINK | 12 | 8 | KERATIN TYPE II |
| | | | 14 EIEQYLNLLLASYLDF | 13 | 16 | KERATIN TYPE I CITOSKELETAL |
| | | | 19 STMQELNSRLASYLDK | 14 | 16 | KERATIN TYPE I CITOSKELETAL |

Fraction 3 contained three bands after total reduction and alkylation as is known in the art. All but two of the peptide sequences showed homology to Keratin Type I or II human proteins. Fraction 4 showed similar results to fraction 3. This amastigote parasite keratin explains the effect of the immunotherapeutic agents of the present invention on psoriasis patients. Many authors have postulated that psoriasis is a disorder in human keratin from epidermal keratinocytes.

EXAMPLE 18

Analysis of Peripheral Blood Lymphocytes with the Flow Cytometer

TABLE 19

Comparison of lymphocyte populations vs. healthy controls in psoriasis patients before treatment.

| | 0 DOSES | CONTROLS | p |
|---|---|---|---|
| | n = 95 | n = 49 | |
| CD4 | 30.7 ± 12.8 | 40.8 ± 9.6 | <0.0001 |
| CD8 | 20.3 ± 9.3 | 28.4 ± 9.7 | <0.0001 |

TABLE 19-continued

Comparison of lymphocyte populations vs. healthy controls in psoriasis patients before treatment.

| | 0 DOSES | CONTROLS | p |
|---|---|---|---|
| CD8 – D4 + | 29 ± 9.9 | 38.9 ± 9.9 | <0.0001 |
| CD3 | 66.7 ± 9.8 | 73.2 ± 9.8 | <0.0004 |
| CD8 + CD3 + | 13.1 ± 7.3 | 19.5 ± 8.6 | <0.0001 |
| HLA + | 34.4 ± 9.5 | 29.8 ± 11.5 | <0.0150 |
| CD8 + HLA – | 11.9 ± 5.9 | 14.7 ± 7 | <0.0129 |
| IgE | 6.7 ± 3.8 | 4.8 ± 2.2 | <0.0061 |
| IgG | 0.8 ± 0.5 | 1.2 ± 0.6 | <0.0026 |

All psoriasis patients, before treatment with the first-generation immunotherapeutic agent, showed peripheral blood lymphocyte populations significantly lower than normal healthy controls, with the exception of HLA and IgE markers, which were present at elevated levels.

TABLE 20

Comparison of lymphocyte populations vs. healthy controls iu psoriasis patients with different degrees of disease severity following PASI values.

| | PASI 1–9 p vs CONTROL | | PASI 10–20 p vs CONTROL | | PASI 21–65 p vs CONTROL | |
|---|---|---|---|---|---|---|
| | n = 38 | n = 49 | n = 32 | n = 49 | n = 25 | n = 49 |
| CD45 | 98.9 ± 1.4 | 0.1283 | 99.0 ± 0.1 | 0.1 | 98.9 ± 1.2 | 0.1 |
| CD4 | 36.6 ± 9.2 | 0.0353 | 34.7 ± 12.6 | 0.0334 | 22.4 ± 10.2 | <0.0001 |
| CD8 | 23.1 ± 8.6 | 0.0047 | 20.0 ± 9.3 | 0.0008 | 18.0 ± 6.7 | <0.0001 |
| CD8 + CD4 + | 2.2 ± 1.5 | 0.6253 | 1.7 ± 1.3 | 0.8163 | 1.6 ± 1.1 | 0.8379 |
| CD8 – CD4 + | 36.3 ± 9.7 | 0.1838 | 28.6 ± 10.4 | 0.0014 | 28.1 ± 8.3 | <0.0001 |
| CD3 | 70.8 ± 9.4 | 0.1100 | 66.3 ± 10.9 | 0.0055 | 62.0 ± 9.8 | <0.0001 |
| CD3 + CD8 – | 57.1 ± 10 | 0.0765 | 51.2 ± 11.6 | 0.9311 | 51.3 ± 7.9 | 0.9802 |

TABLE 20-continued

Comparison of lymphocyte populations vs. healthy controls in psoriasis patients with different degrees of disease severity following PASI values.

|  | PASI 1–9 | p vs CONTROL | PASI 10–20 | p vs CONTROL | PASI 21–65 | p vs CONTROL |
|---|---|---|---|---|---|---|
|  | n = 38 | n = 49 | n = 32 | n = 49 | n = 25 | n = 49 |
| CD8 + CD3 + | 15.5 ± 8.5 | 0.0184 | 14.0 ± 8.5 | 0.0100 | 12.8 ± 6.9 | 0.0030 |
| CD8 + CD3 − | 6.8 ± 3.6 | 0.4337 | 4.7 ± 2.6 | 0.1182 | 4.4 ± 3.9 | 0.0344 |
| TCR | 2.1 ± 1 | 0.4337 | 2.1 ± 1.7 | 0.3633 | 2.1 ± 0.8 | 0.1441 |
| HLA + | 32.5 ± 7.9 | 0.3389 | 32.8 ± 7.7 | 0.2202 | 35.8 ± 9.2 | 0.0424 |
| CD8 + HLA + | 8.4 ± 4.9 | 0.0574 | 7.6 ± 5.2 | 0.0418 | 12.8 ± 9.6 | 0.4227 |
| CD8 + HLA − | 12.1 ± 4.6 | 0.0483 | 12.6 ± 5.8 | 0.1801 | 9.8 ± 3.7 | 0.0039 |
| CD19 | 7.4 ± 3.6 | 0.8455 | 8.4 ± 4.3 | 0.2806 | 8.0 ± 3.5 | 0.5216 |

Peripheral blood lymphocyte populations were studied in psoriasis patients before treatment with the first-generation immunotherapeutic agent. Patients were distributed according to severity of the disease, tabulated according to PASI values. The results are shown in Table 20. As PASI values increased in psoriasis patients, peripheral blood lymphocyte populations of CD4+, CD8+, CD8−CD4+, CD3, CD8+CD3+, CD8+CD3−, CD8+HLA− decreased while populations of HLA+ increased relative to healthy controls. In the group with PASI 1–9, only four lymphocyte populations were lower than control values, while in the group with PASI 21–65, seven lymphocyte populations were lower than values for healthy controls. This suggests that lymphocytes migrate from peripheral blood to dermis and epidermis in the skin of psoriatic patients to induce the chronic inflammation characteristic of the disease.

TABLE 22

Comparison of lymphocyte populations vs. healthy controls in psoriasis patients with total remission of lesions after more than 10 doses of first-generation immunotherapeutic agent.
Cured patients >10 DOSES of immunotherapeutic agent

|  | n = 49 | p vs. CONTROL n = 49 |
|---|---|---|
| CD45 | 99.2 ± 0.4 | 0.1283 |
| CD45 RO | 43.9 ± 7.0 | 0.5406 |
| CD4 | 43.2 ± 9.4 | 0.7561 |
| CD8 | 27.3 ± 6.6 | 0.3985 |
| CD8 + CD4 + | 1.4 ± 0.7 | 0.2537 |
| CD8 − CD4 + | 40.5 ± 6.6 | 0.9923 |
| CD3 | 70.0 ± 9.5 | 0.063 |
| CD3 + CD8 − | 51.7 ± 9.2 | 0.5583 |
| CD8 + CD3 + | 16.2 ± 5.0 | 0.0634 |
| HLA + | 39.1 ± 9.6 | 0.0108 |
| CD8HLA + | 14.9 ± 7.1 | 0.0766 |
| CD8HLA − | 12.4 ± 4.0 | 0.1113 |
| CD19 | 10.9 ± 4.9 | 0.0031 |

TABLE 21

Comparison of lymphocyte populations in psoriasis patients with different degrees of disease severity.

|  | PASI [1–9] | PASI [10–20] | p | I.C. 95% | PASI [>20] | p | I.C. 95% |
|---|---|---|---|---|---|---|---|
| CD4+ | 36.6 ± 9.2 | 30.5 ± 13.9 | <0.4982 |  | 22.4 ± 10.2 | <0.0001 | [−19.1 a −9.7] |
| CD8+ | 23.1 ± 8.6 | 23.8 ± 13.5 | <0.1984 |  | 18.0 ± 6.7 | <0.039 | [−9.3 a −1.8] |
| CD8+CD4+ | 2.2 ± 1.5 | 2.0 ± 2.1 | <0.2139 |  | 1.6 ± 1.1 | <0.0001 | [34.2 a 44.5] |
| CD8−CD4+ | 36.3 ± 9.7 | 26.7 ± 12.1 | <0.0330 | [−14.7 a −0.6] | 23.1 ± 8.3 | <0.0001 | [−20 a −7.5] |
| CD3 | 70.8 ± 9.4 | 67.5 ± 11.5 | <0.0792 |  | 62.0 ± 9.8 | <0.0002 | [−15.5 a −4.9] |
| CD3+CD8− | 57.1 ± 10.0 | 50 ± 14.2 | <0.0476 | [−11.9 a 0.05] | 51.3 ± 7.9 | <0.0118 | [−13.9 a −1.8] |
| CD8+HLA− | 12.1 ± 4.6 | 13.0 ± 6.1 | <0.07337 |  | 9.8 ± 3.7 | <0.0310 | [−4.4 a −0.21] |
| IGA+ | 5.1 ± 2.9 | 7.4 ± 3.6 | <0.0443 | [0.06 a 4.6] | 10.5 ± 7.0 | <0.0001 | [5.3 a 12.8] |
| IGD+ | 11.5 ± 3.5 | 16.4 ± 9 | <0.0387 | [0.17 a 6.25] | 14.9 ± 6.0 | <0.1462 |  |

There are significant differences in lymphocyte populations between patients with different PASI values. Comparison of 1–9 and 10–20 groups shows four lymphocyte populations with lower values in the group with a more severe psoriasis. Comparison between groups with PASI 1–9 and PASI greater than 20 units showed seven lymphocyte populations with lower values in the group with severe psoriatic lesions. IgA+ lymphocytes were higher in the group with more severe disease.

After clinical remission of lesions all peripheral blood lymphocyte populations returned to normal values, similar to healthy controls. Only HLA+ and CD19 lymphocyte populations had higher values than normal controls, probably because of lymphocyte stimulation after immunotherapeutic agent treatment.

The foregoing description of specific embodiments is merely illustrative, and various modifications may be made without deviating from the spirit and scope of the present invention, which is limited only by the following claims.

What is claimed is:

1. An immunotherapeutic agent capable of eliciting an immune response to result in abatement of the clinical symptoms of psoriasis, said agent comprising a purified protein extract wherein said purified extract is isolated by diethylaminoethyl Sephadex chromatography of a Nonidet P-40 insoluble particulate antigen fraction derived from isolated killed cells of amastigotes from at least one species of the Leishmania genus, said particulate antigen fraction solubilized with 8 M urea and 0.025 M Tris[hydroxymethyl] aminomethane pH 8.3 applied to diethylaminoethyl Sephadex and eluted with a solution comprising 0.1 M. sodium chloride, 8 M urea and 0.025 M. Tris[hydroxymethyl] aminomethane pH 8.3, said purified protein extract consisting of polypeptides having apparent molecular weights after total reduction and allylation of 73, 80 and 82 kDa.

2. The immunotherapeutic agent of claim 1, wherein the species is *Leishmania amazonensis*.

3. The immunotherapeutic agent of claim 1, wherein the species is *Leishmania venezuelensis*.

4. The immunotherapeutic agent of claim 1, wherein the species is *Leishmania brasiliensis*.

5. The immunotherapeutic agent of claim 1, wherein the species is *Leishmania chagasi*.

6. The immunotherapeutic agent of claim 1, wherein the species are *Leishmania amazonensis, Leishmania venezuelensis, Leishmania brasiliensis* and *Leishmania chagasi*.

7. The immunotherapeutic agent of claim 1, wherein the 73 kDa polypeptide comprises the amino acid sequences set forth in SEQ ID NOS: 1, 5 and 6, wherein the 80 kDa polypeptide comprises the amino acids sequences set forth in SEQ ID NOS: 1, 3 and 4 and wherein the 82 kDa polypeptide comprises the amino acids sequences set forth in SEQ ID NOS: 1 and 2.

8. The immunotherapeutic agent of any one of claims 1–7 further comprising an adjuvant.

9. The immunotherapeutic agent of claim 8, wherein the adjuvant is alumina.

10. An immunotherapeutic agent capable of eliciting an immune response to result in abatement of the clinical symptoms of psoriasis, said agent comprising a purified protein extract wherein said purified extract is isolated by diethylaminoethyl Sephadex chromatography of a Nonidet P-40 insoluble particulate antigen fraction derived from isolated killed cells of amastigotes from at least one species of the Leishmania genus, said particulate antigen fraction solubilized with 8 M urea and 0.025 M Tris[hydroxymethyl] aminomethane pH 8.3 applied to diethylaminoethyl Sephadex and eluted with a solution comprising 0.15 M. sodium chloride, 8 M urea and 0.025 M. Tris[hydroxymethyl] aminomethane pH 8.3, said purified protein extract consisting of polyepeptides having apparent molecular weights after total reduction and alkylation of 73, 80 and 82 kDa.

11. The immunotherapeutic agent of claim 10, wherein the species is *Leishmania amazonensis*.

12. The immunotherapeutic agent of claim 10, wherein the species is *Leishmania venezuelensis*.

13. The immunotherapeutic agent of claim 10, wherein the species is *Leishmania brasiliensis*.

14. The immunotherapeutic agent of claim 10, wherein the species is *Leishmania chagasi*.

15. The immunotherapeutic agent of claim 10, wherein the species are *Leishmania amazonensis, Leishmania venezuelensis, Leishmania brasiliensis* and *Leishmania chagasi*.

16. The immunotherapeutic agent of claim 10, wherein the 73 kDa polypeptide comprises the amino acid sequences set forth in SEQ ID NOS:11, 12, 13 and 14, wherein the 80 kDa polypeptide comprises the amino acids sequences set forth in SEQ ID NOS: 1, 3 and 10 and wherein the 82 kDa polypeptide comprises the amino acids sequences set forth in SEQ ID NOS: 7, 8 and 9.

17. The immunotherapeutic agent of any one of claims 10–16 further comprising an adjuvant.

18. The immunotherapeutic agent of claim 17, wherein the adjuvant is alumina.

\* \* \* \* \*

SEQUENCE LISTING

<160> NUMBER OF SEQ ID NOS: 14

<210> SEQ ID NO 1
<211> LENGTH: 7
<212> TYPE: PRT
<213> ORGANISM: Leishmania

<400> SEQUENCE: 1

Tyr Glu Asp Glu Ile Asn Lys
1               5

<210> SEQ ID NO 2
<211> LENGTH: 9
<212> TYPE: PRT
<213> ORGANISM: Leishmania

<400> SEQUENCE: 2

Ala Gln Tyr Glu Asp Ile Ala Gln Lys
1               5

<210> SEQ ID NO 3
<211> LENGTH: 16
<212> TYPE: PRT
<213> ORGANISM: Leishmania

<400> SEQUENCE: 3

Glu Ile Glu Thr Tyr His Asn Leu Leu Glu Gly Gly Gln Glu Asp Phe
1               5                   10                  15

<210> SEQ ID NO 4
<211> LENGTH: 9
<212> TYPE: PRT
<213> ORGANISM: Leishmania

<400> SEQUENCE: 4

Ala Gln Tyr Glu Asp Ala Ile Gln Lys
1               5

<210> SEQ ID NO 5
<211> LENGTH: 7
<212> TYPE: PRT
<213> ORGANISM: Leishamania

<400> SEQUENCE: 5

Ala Glu Ala Glu Ser Leu Tyr
1               5

<210> SEQ ID NO 6
<211> LENGTH: 12
<212> TYPE: PRT
<213> ORGANISM: Leishmania

<400> SEQUENCE: 6

Asn Tyr Ser Pro Tyr Tyr Asn Thr Ile Asp Asp Leu
1               5                   10

<210> SEQ ID NO 7
<211> LENGTH: 10
<212> TYPE: PRT
<213> ORGANISM: Leishmania

<400> SEQUENCE: 7

Ala Glu Ala Glu Ser Leu Tyr Gln Ser Lys

-continued

```
1               5                   10
```

<210> SEQ ID NO 8
<211> LENGTH: 9
<212> TYPE: PRT
<213> ORGANISM: Leishmania

<400> SEQUENCE: 8

```
Ala Thr Asn Ala Glu Asn Glu Phe Val
1               5
```

<210> SEQ ID NO 9
<211> LENGTH: 16
<212> TYPE: PRT
<213> ORGANISM: Leishmania
<220> FEATURE:
<221> NAME/KEY: Xaa
<222> LOCATION: (1)..(3)
<223> OTHER INFORMATION: Xaa is an unknown amino acid.

<400> SEQUENCE: 9

```
Xaa Xaa Xaa Ser Glu Leu Asn Arg Val Ile Gln Arg Leu Arg Ser Ile
1               5                   10                  15
```

<210> SEQ ID NO 10
<211> LENGTH: 8
<212> TYPE: PRT
<213> ORGANISM: Leishmania

<400> SEQUENCE: 10

```
Ala Gln Tyr Glu Asp Tyr Ala Gln
1               5
```

<210> SEQ ID NO 11
<211> LENGTH: 8
<212> TYPE: PRT
<213> ORGANISM: Leishmania

<400> SEQUENCE: 11

```
Tyr Glu Asp Glu Ile Asn Asn Lys
1               5
```

<210> SEQ ID NO 12
<211> LENGTH: 8
<212> TYPE: PRT
<213> ORGANISM: Leishmania

<400> SEQUENCE: 12

```
Lys Tyr Glu Asp Glu Ile Asn Lys
1               5
```

<210> SEQ ID NO 13
<211> LENGTH: 16
<212> TYPE: PRT
<213> ORGANISM: Leishmania

<400> SEQUENCE: 13

```
Glu Ile Glu Gln Tyr Leu Asn Leu Leu Leu Ala Ser Tyr Leu Asp Phe
1               5                   10                  15
```

<210> SEQ ID NO 14
<211> LENGTH: 16
<212> TYPE: PRT
<213> ORGANISM: Leishmania

<400> SEQUENCE: 14

-continued

```
Ser Thr Met Gln Glu Leu Asn Ser Arg Leu Ala Ser Tyr Leu Asp Lys
1               5                   10                  15
```